United States Patent
Ehricht et al.

(10) Patent No.: US 9,316,640 B2
(45) Date of Patent: Apr. 19, 2016

(54) DEVICES AND METHODS FOR DETECTION OF PANTON-VALENTINE LEUKOCIDIN (PVL)

(71) Applicant: Alere San Diego, Inc., San Diego, CA (US)

(72) Inventors: Ralf Ehricht, Jena (DE); Stefan Monecke, Jena (DE); John J. Rejman, Falmouth, ME (US); Joseph Buechler, Carlsbad, CA (US)

(73) Assignee: Alere San Diego, Inc., San Diego, CA (US)

( * ) Notice: Subject to any disclaimer, the term of this patent is extended or adjusted under 35 U.S.C. 154(b) by 0 days.

(21) Appl. No.: 14/355,843

(22) PCT Filed: Nov. 9, 2012

(86) PCT No.: PCT/US2012/064535
§ 371 (c)(1),
(2) Date: May 1, 2014

(87) PCT Pub. No.: WO2013/071175
PCT Pub. Date: May 16, 2013

(65) Prior Publication Data
US 2014/0303033 A1 Oct. 9, 2014

Related U.S. Application Data

(60) Provisional application No. 61/714,649, filed on Oct. 16, 2012, provisional application No. 61/617,974, filed on Mar. 30, 2012, provisional application No. 61/561,767, filed on Nov. 18, 2011, provisional application No. 61/558,848, filed on Nov. 11, 2011.

(51) Int. Cl.
*G01N 33/569* (2006.01)
*G01N 33/53* (2006.01)
*C07K 16/12* (2006.01)

(52) U.S. Cl.
CPC ...... *G01N 33/56938* (2013.01); *C07K 16/1271* (2013.01); *G01N 33/53* (2013.01)

(58) Field of Classification Search
CPC ............... G01N 33/56938; G01N 2333/31; G01N 33/5306; G01N 33/5375; G01N 33/54393; G01N 2469/10; G01N 2500/10; G01N 2800/56; G01N 33/5014; G01N 33/5035; G01N 33/5047; G01N 33/68
See application file for complete search history.

(56) References Cited

U.S. PATENT DOCUMENTS

| | | | |
|---|---|---|---|
| 7,879,624 | B2 | 2/2011 | Sharrock |
| 7,947,808 | B2 | 5/2011 | Ohishi et al. |
| 8,029,982 | B2 | 10/2011 | Kingsmore et al. |
| 8,124,107 | B2 | 2/2012 | Hook et al. |
| 8,217,150 | B2 | 7/2012 | Ohishi et al. |
| 2009/0130115 | A1 | 5/2009 | Hook et al. |

(Continued)

OTHER PUBLICATIONS

Löffler et al., "*Staphylococcus aureus* Panton-Valentine Leukocidin is a Very Potent Cytotoxic Factor for Human Neutrophils," *PLOS Pathogens* (2010), 6(1):1-12 e1000715.

(Continued)

*Primary Examiner* — Padma V Baskar
(74) *Attorney, Agent, or Firm* — DLA Piper LLP (US)

(57) ABSTRACT

The present invention provides methods and devices for detecting the presence of biomolecules in a biological sample, such as PVL, PBP2a and SPA.

14 Claims, 17 Drawing Sheets

(56) References Cited

U.S. PATENT DOCUMENTS

2010/0129839 A1    5/2010    Badiou et al.
2011/0223614 A1    9/2011    Ohishi et al.
2011/0251162 A1   10/2011   Liu et al.

OTHER PUBLICATIONS

Monecke et al., "Rapid Detection of Panton-Valentine Leukocidin in *Staphylococcus aureus* Cultures by Use of a Lateral Flow Assay Based on Monoclonal Antibodies," *J. Clin. Microbiol.* (2013), 51(2):487-495.

Nguyen et al., "Detection and Quantification of Panton-Valentine Leukocidin in *Staphylococcus aureus* Cultures by ELISA and Western Blotting: Diethylpyrocarbonate Inhibits Binding of Protein A to IgG," *J. Immunol. Methods* (2010), 356(1-2):1-9.

Brown, E.L. et al.: "*Identification of a T-cell epitope in the Staphylococcus aureus Panton-Valentine LukS-PV component*"; Open Journal of Immunology, vol, 2, No. 3, Nov. 1, 2012, pp. 111-115.

| Strain: | CC1-MSSA | CC1-MRSA-IV USA400 | CC5-MRSA-V | CC5-MSSA | CC5-MRSA-IV Paediatric clone | ST8-MRSA-IV USA300 | ACME-neg. USA300 |
|---|---|---|---|---|---|---|---|
| Isolates tested: | 1 | 2 | 1 | 4 | 1 | 18 | 4 |
| Lowest PVL Yield (F component, ng/mL) | | 576.3 | | 39.6 | | 338.4 | 1667.0 |
| Highest PVL yield (F component, ng/mL) | | 956.6 | | 1733.0 | | 7995.5 | 6673.0 |
| Average PVL yield (F component, ng/mL) | 1004.0 | 766.5 | 764.2 | 748.8 | 548.2 | 3966.3 | 4021.0 |

| Strain: | CC22-MSSA | ST22-MRSA-IV | CC25-MSSA | CC30-MSSA | CC5-MRSA-IV SWPP Clone | ST30-MRSA-IV WA MRSA-55/56 | CC59-MRSA-V |
|---|---|---|---|---|---|---|---|
| Isolates tested: | 6 | 2 | 3 | 16 | 7 | 3 | 1 |
| Lowest PVL Yield (F component, ng/mL) | 366.0 | 179.8 | 1196.0 | 52.0 | 203.3 | 401.2 | |
| Highest PVL yield (F component, ng/mL) | 4486.5 | 2234.0 | 2005.0 | 6459.0 | 2770.0 | 2533.0 | |
| Average PVL yield (F component, ng/mL) | 2112.3 | 1206.9 | 1575.3 | 737.0 | 828.9 | 1482.7 | 383.8 |

| Strain: | CC80-MSSA | CC80-MRSA-IV European caMRSA | CC8-MSSA | CC8-MRSA-IV | CC89-MSSA | ST89-MRSA-IV Queensland Clone | ST98952-MRSA-V(?), Taiwan Cl. |
|---|---|---|---|---|---|---|---|
| Isolates tested: | 1 | 7 | 2 | 1 | 6 | 10 | 4 |
| Lowest PVL Yield (F component, ng/mL) | | 149.1 | 248.0 | | 4974.2 | 402.1 | 652.1 |
| Highest PVL yield (F component, ng/mL) | | 477.8 | 1457.0 | | 10025.4 | 12170.4 | 5720.0 |
| Average PVL yield (F component, ng/mL) | 631.8 | 259.4 | 852.5 | 2971.0 | 6482.7 | 5285.3 | 2916.9 |

| Strain: | CC96/154-MSSA | CC121-MSSA | CC152-MSSA | CC152-MRSA-V | ST398-MRSA-V | ST398-MSSA | |
|---|---|---|---|---|---|---|---|
| Isolates tested: | 1 | 5 | 2 | 2 | 2 | 2 | |
| Lowest PVL Yield (F component, ng/mL) | | 532.8 | 330.0 | 640.5 | 669.5 | 0.0 | |
| Highest PVL yield (F component, ng/mL) | | 2295.0 | 2685.0 | 868.1 | 892.9 | 0.0 | |
| Average PVL yield (F component, ng/mL) | 211.3 | 1183.7 | 1507.5 | 754.3 | 781.2 | 0.0 | |

FIG. 1A

| ISOLATE | STRAIN COLLECTION | STRAIN AFFILIATION | CATEGORY ACCORDING TO ANTIBODY ARRAY MEASUREMENTS | LATERAL FLOW TEST INTERPR. |
|---|---|---|---|---|
| 05V1343 | A20 | CC121-MSSA [PVL+] | HIGH LEVEL (>4,500 ng/mL) | POSITIVE/VALID |
| 06V15104 | X54 | CC22-MSSA [PVL+] | HIGH LEVEL (>4,500 ng/mL) | POSITIVE/VALID |
| AUSTR.03-16790 | Z112 | ST93-MRSA-IV [PVL+] Queensland Clone | HIGH LEVEL (>4,500 ng/mL) | POSITIVE/VALID |
| AUSTR.05-RBH-1-4 | Z492 | ST93-MRSA-IV [PVL+] Queensland Clone | HIGH LEVEL (>4,500 ng/mL) | POSITIVE/VALID |
| AUSTR.9559120L | Z487 | ST93-MSSA [PVL+] | HIGH LEVEL (>4,500 ng/mL) | POSITIVE/VALID |
| USA300-FPR3757 | Z530 | ST8-MRSA-IV, USA 300 | HIGH LEVEL (>4,500 ng/mL) | POSITIVE/VALID |
| 05V08535 | O36 | CC80/154-MSSA [PVL+] | LOW LEVEL (<450 ng/mL) | POSITIVE/VALID |
| 05V12517 | A52 | CC9-MSSA [PVL+] | LOW LEVEL (<450 ng/mL) | POSITIVE/VALID |
| 08V10366 | X120 | CC22-MSSA [PVL+] | LOW LEVEL (<450 ng/mL) | POSITIVE/VALID |
| 08V04989 | A124 | CC30-MSSA [PVL+] | LOW LEVEL (<450 ng/mL) | POSITIVE/VALID |
| ATCC25923-Saarbrucken | R67 | CC30-MSSA [PVL+] | LOW LEVEL (<450 ng/mL) | POSITIVE/VALID |
| SA RI-MRSA-0723 | Z362 | ST22-MRSA-IV [PVL+] | LOW LEVEL (<450 ng/mL) | POSITIVE/VALID |
| JENA-FLI-14-TGD-1737-916 | V571 | CC133-MSSA | BOVINE LEUKOCIDIN (lukM/lukF-PV-P83) | POSITIVE/VALID |
| JENA-FLI-KS-01-22 | V572 | CC151-MSSA | BOVINE LEUKOCIDIN (lukM/lukF-PV-P83) | POSITIVE/VALID |
| JENA-FLI-KS-02-141 | V573 | CC151-MSSA | BOVINE LEUKOCIDIN (lukM/lukF-PV-P83) | POSITIVE/VALID |
| JENA-FLI-KS-05-159 | V574 | CC479-MSSA | BOVINE LEUKOCIDIN (lukM/lukF-PV-P83) | POSITIVE/VALID |
| JENA-FLI-KS-05-234 | V575 | CC479-MSSA | BOVINE LEUKOCIDIN (lukM/lukF-PV-P83) | POSITIVE/VALID |
| JENA-FLI-Ziege-16B | V136 | CC133-MSSA | BOVINE LEUKOCIDIN (lukM/lukF-PV-P83) | POSITIVE/VALID |
| COL | R11 | CC8-MRSA-I | PVL NEGATIVES | NEGATIVE/VALID |
| MSSA476 | R20 | CC1-MSSA | PVL NEGATIVES | NEGATIVE/VALID |
| MW2 | R4 | CC5-MRSA-II | PVL NEGATIVES | NEGATIVE/VALID |
| N315 | R17 | CC5-MRSA-AA | PVL NEGATIVES | NEGATIVE/VALID |
| NCTC 8325 | R15 | CC8-MSSA | PVL NEGATIVES | FALSE POSITIVE/VALID |
| ATCC 35984, NA RSA 101 | R21 | Staph. epidermidis ? | PVL NEGATIVES | NEGATIVE/VALID |

FIG. 2

| Capture Antibody | Antigen | Detection antibody → | 1031 | 1061 | 1101 | 1321 | 1401 | 1451 | 1631 | 1771 | 1841 | 1881 |
|---|---|---|---|---|---|---|---|---|---|---|---|---|
| 1881 | Culture supernatant lukF-P83 | | ± | ± | ∘ | ∘ | ∘ | ∘ | ± | ‡ | ± | ∘ | ± |
| | Culture supernatant ATCC25923 | | ± | ± | ± | + | ‡ | + | ± | ‡ | ‡ | ‡ | ± |
| | Recombinant LukF | | ∘ | ∘ | ∘ | ∘ | ∘ | ∘ | ∘ | + | ∘ | ∘ |
| 1841 | Culture supernatant lukF-P83 | | ± | ± | ‡ | ∘ | ‡ | ± | ± | ± | ± | + | ± |
| | Culture supernatant ATCC25923 | | ‡ | + | ‡ | ‡ | ‡ | ‡ | ± | ‡ | ‡ | ‡ | ± |
| | Recombinant LukF | | + | ∘ | ‡ | ‡ | ‡ | + | ∘ | ‡ | + | + | ∘ |
| 1771 | Culture supernatant lukF-P83 | | ± | ± | ∘ | ± | + | ± | ± | ± | ± | ∘ | ± |
| | Culture supernatant ATCC25923 | | ‡ | + | ‡ | ‡ | ‡ | ‡ | ± | ‡ | ‡ | ‡ | ± |
| | Recombinant LukF | | + | ∘ | + | ‡ | ‡ | ± | ∘ | ‡ | + | + | ∘ |
| 1711 | Culture supernatant lukF-P83 | | ± | ∘ | ∘ | ∘ | ∘ | ∘ | ∘ | ∘ | ∘ | ∘ | ± |
| | Culture supernatant ATCC25923 | | ∘ | + | + | ∘ | ± | ‡ | ∘ | ± | ‡ | ‡ | ± |
| | Recombinant LukF | | ∘ | ∘ | ∘ | ∘ | ∘ | ‡ | ∘ | ∘ | + | ‡ | ∘ |
| 1631 | Culture supernatant lukF-P83 | | ∘ | ∘ | ∘ | ∘ | ∘ | ∘ | ∘ | ∘ | ∘ | ∘ | ± |
| | Culture supernatant ATCC25923 | | ∘ | ∘ | ∘ | ∘ | ± | ± | ∘ | ± | ± | ± |
| | Recombinant LukF | | ∘ | ∘ | ∘ | ∘ | ∘ | ∘ | ∘ | ∘ | ∘ | ∘ |
| 1451 | Culture supernatant lukF-P83 | | ± | ∘ | ∘ | ∘ | + | ∘ | ∘ | ± | ± | ∘ | ± |
| | Culture supernatant ATCC25923 | | ‡ | ± | ‡ | ‡ | ‡ | ‡ | ± | ‡ | ‡ | ‡ | ± |
| | Recombinant LukF | | ± | ∘ | + | ‡ | ‡ | ∘ | ∘ | ‡ | ± | ∘ | ∘ |
| 1401 | Culture supernatant lukF-P83 | | ∘ | ∘ | ‡ | ∘ | ‡ | ‡ | ∘ | ∘ | ‡ | ‡ | ∘ |
| | Culture supernatant ATCC25923 | | + | + | ± | ± | ‡ | ‡ | ∘ | + | ‡ | ‡ | ± |
| | Recombinant LukF | | ± | ∘ | ∘ | ∘ | ∘ | + | ∘ | ∘ | + | ‡ | ∘ |
| 1321 | Culture supernatant lukF-P83 | | ∘ | ∘ | ∘ | ∘ | ∘ | ∘ | ± | ∘ | ∘ | ∘ | ∘ |
| | Culture supernatant ATCC25923 | | ± | ‡ | ‡ | ± | + | ‡ | ± | + | ‡ | ‡ | ± |
| | Recombinant LukF | | ∘ | ± | ∘ | ∘ | ∘ | ‡ | ∘ | ∘ | ‡ | ‡ | ∘ |
| 1101 | Culture supernatant lukF-P83 | | ∘ | ∘ | ± | ∘ | ‡ | ± | ∘ | ∘ | ± | ‡ | ∘ |
| | Culture supernatant ATCC25923 | | + | + | ± | ‡ | ‡ | ‡ | ∘ | ‡ | ‡ | ‡ | ± |
| | Recombinant LukF | | ∘ | ∘ | ∘ | ± | ∘ | ‡ | ∘ | ± | + | ‡ | ∘ |
| 1061 | Culture supernatant lukF-P83 | | ∘ | ∘ | ∘ | ∘ | ∘ | ∘ | ∘ | ∘ | ∘ | ∘ | ∘ |
| | Culture supernatant ATCC25923 | | ∘ | ∘ | ± | ± | + | ∘ | ∘ | + | ∘ | ∘ | ∘ |
| | Recombinant LukF | | ∘ | ∘ | ∘ | ∘ | ∘ | ∘ | ∘ | ∘ | ∘ | ∘ |
| 1031 | Culture supernatant lukF-P83 | | ∘ | ∘ | ∘ | ∘ | ∘ | ∘ | ∘ | ∘ | ∘ | ∘ | ± |
| | Culture supernatant ATCC25923 | | ± | ± | + | + | ‡ | ∘ | ‡ | ‡ | ‡ | ± |
| | Recombinant LukF | | ∘ | ∘ | ∘ | ∘ | + | ± | ∘ | ∘ | + | + | ∘ |

FIG. 3

>CL0001 Z1 01401 Light chain (DNA)
GACGTTGTGATGTCACAGTCTCCATCCTCCCTGACTGTGACAGCAGGAGAGAAGGTCACTAT
GAGCTGCAAGTCCAGTCAGAGTCTGTTACTCAGTGGAAATCAAAAGAACCTCTTGACCTGGT
TCCAGCAGAAACCAGGGCAGCCTCCTAAACTGTTGATCTACTGGGCATCCACTAGGGAATCT
GGGGTCCCTGATCGCTTCACAGGCAGTGGATCTGGAACAGATTTCACTCTCACCATCAGCAG
TGTGCAGGCTGAAGACCTGGCAGTTTATTACTGTCAGAATGATTATAATTATCCGTACACGT
TCGGAGGGGGGACCAAGCTGGAAATAAAACGGGCTGATGCTGCACCAACTGTATCCATCTTC
CCACCATCCAGTGAGCAGTTAACATCTGGAGGTGCCTCAGTCGTGTGCTTCTTGAACAACTT
CTACCCCAAAGACATCAATGTCAAGTGGAAGATTGATGGCAGTGAACGACAAAATGGCGTCC
TGAACAGTTGGACTGATCAGGACAGCAAAGACAGCACCTACAGCATGAGCAGCACCCTCACG
TTGACCAAGGACGAGTATGAACGACATAACAGCTATACCTGTGAGGCCACTCACAAGACATC
AACTTCACCCATTGTCAAGAGCTTCAACAGGAATGAGTCT (SEQ ID NO: 1)

>CL0001 Z1 01401 Heavy chain (DNA)
CAGGTCCAGCTGCAGCAGTCTGGGCCTCAGCTGGTTAGGCCTGGGGCTTCAGTGAAGATATC
CTGCAAGGCTTCTGGTCACTCATTCACCACCTACTGGATGCACTGGGTGAAGCAGAGGCCTG
GACAAGGTCTTGAGTGGATTGGCATGATTGATCCTTCCGATAGTGAAACTAGGTTAAATCAG
AAGTTCAAGGACAAGGCCACATTGACTGTAGACAAATCCTCCAGCACAGTCTACATGCAACT
CAGCAGCCCGACATCTGAAGACTCTGTGGTCTATTACTGTGCAAGCTACTATGGCAATTCTA
TGGACTACTGGGGTCAAGGAACCTCAGTCACCGTCTCCTCAGCCAAAACGACACCCCCATCT
GTCTATCCACTGGCCCCTGGATCTGCTGCCCAAACTAACTCCATGGTGACCCTGGGATGCCT
GGTCAAGGGCTATTTCCCTGAGCCAGTGACAGTGACCTGGAACTCTGGATCCCTGTCCAGCG
GTGTGCACACCTTCCCAGCTGTCCTGCAGTCTGACCTCTACACTCTGAGCAGCTCAGTGACT
GTCCCCTCCAGCACCTGGCCCAGCGAGACCGTCACCTGCAACGTTGCCCACCCGGCCAGCAG
CACCAAGGTGGACAAGAAAATTGTGCCCAGGGATTGTCATCATCACCATCACCATCACTAA
(SEQ ID NO: 3)

>CL0001 Z1 01401 Light chain
DVVMSQSPSSLTVTAGEKVTMSCKSSQSLLLSGNQKNLLTWFQQKPGQPPKLLIYWASTRES
GVPDRFTGSGSGTDFTLTISSVQAEDLAVYYCQNDYNYPYTFGGGTKLEIKRADAAPTVSIF
PPSSEQLTSGGASVVCFLNNFYPKDINVKWKIDGSERQNGVLNSWTDQDSKDSTYSMSSTLT
LTKDEYERHNSYTCEATHKTSTSPIVKSFNRNES (SEQ ID NO: 2)

>CL0001 Z1 01401 Heavy chain
QVQLQQSGPQLVRPGASVKISCKASGHSFTTYWMHWVKQRPGQGLEWIGMIDPSDSETRLNQ
KFKDKATLTVDKSSSTVYMQLSSPTSEDSVVYYCASYYGNSMDYWGQGTSVTVSSAKTTPPS
VYPLAPGSAAQTNSMVTLGCLVKGYFPEPVTVTWNSGSLSSGVHTFPAVLQSDLYTLSSSVT
VPSSTWPSETVTCNVAHPASSTKVDKKIVPRDCHHHHHH (SEQ ID NO: 4)

FIG. 4

>CL0001 Z1 01841 Light chain (DNA)
GATGTTGTGGTGACTCAAACTCCACTCTCCCTGCCTGTCAGTCTTGGAGATCAAGCCTCCAT
CTCTTGCAGATCTAGTCAGAGCCTTGTACACAGTGATGGAAACACCTATTTACATTGGTACC
TGCAGAAGCCAGGCCAGTCTCCAAAGCTCCTGATCTACAAAGTTTCCAACCGATTTTCTGGG
GTCCCAGACAGGTTCAGTGGCAGTGGATCAGGGACAGATTTCACACTCAAGATCAGCAGAGT
GGAGGCTGAAGATCTGGGAGTTTATTTCTGCTCTCAAAATACACATGTTCCATTCACATTCG
GCTCGGGGACAAAGTTGGAAATAAAACGGGCTGATGCTGCACCAACTGTATCCATCTTCCCA
CCATCCAGTGAGCAGTTAACATCTGGAGGTGCCTCAGTCGTGTGCTTCTTGAACAACTTCTA
CCCCAAAGACATCAATGTCAAGTGGAAGATTGATGGCAGTGAACGACAAAATGGCGTCCTGA
ACAGTTGGACTGATCAGGACAGCAAAGACAGCACCTACAGCATGAGCAGCACCCTCACGTTG
ACCAAGGACGAGTATGAACGACATAACAGCTATACCTGTGAGGCCACTCACAAGACATCAAC
TTCACCCATTGTCAAGAGCTTCAACAGGAATGAGTCT (SEQ ID NO: 5)

>CL0001 Z1 01841 Heavy chain (DNA)
GAGATCCAGCTGCAGCAGTCTGGAGCTGAGCTGGGGAGGCCTGGGTCCTCAGTGAAGCTGTC
CTGCAAGACTTCTGGATATACTTTCACAAACTTTTATATAACCTGGCTGAAACAGAGGCCTG
GACAGGGCCTGGAATGGATTGGATTTATTTATCCTGGAAATGGTTATACTGCATACAATGAG
AAATTCCAGGGAGAGGCCACACTGACTTCAGACACATCTTCCAGCACAGCCTACATGCACCT
CAGAAGCCTGACATCTGAGGACTCTGCAATCTATTTCTGTGCAAGACTGGGACGAAATGAAG
TTGACTACTGGGGCCAAGGCACCACTCTCACAGTCTCCTCAGCCAAAACGACACCCCCATCT
GTCTATCCACTGGCCCCTGGATCTGCTGCCCAAACTAACTCCATGGTGACCCTGGGATGCCT
GGTCAAGGGCTATTTCCCTGAGCCAGTGACAGTGACCTGGAACTCTGGATCCCTGTCCAGCG
GTGTGCACACCTTCCCAGCTGTCCTGCAGTCTGACCTCTACACTCTGAGCAGCTCAGTGACT
GTCCCCTCCAGCACCTGGCCCAGCGAGACCGTCACCTGCAACGTTGCCCACCCGGCCAGCAG
CACCAAGGTGGACAAGAAAATTGTGCCCAGGGATTGTCATCATCACCATCACCATCACTAA
(SEQ ID NO: 7)

>CL0001 Z1 01841 Light chain
DVVVTQTPLSLPVSLGDQASISCRSSQSLVHSDGNTYLHWYLQKPGQSPKLLIYKVSNRFSG
VPDRFSGSGSGTDFTLKISRVEAEDLGVYFCSQNTHVPFTFGSGTKLEIKRADAAPTVSIFP
PSSEQLTSGGASVVCFLNNFYPKDINVKWKIDGSERQNGVLNSWTDQDSKDSTYSMSSTLTL
TKDEYERHNSYTCEATHKTSTSPIVKSFNRNES (SEQ ID NO: 6)

>CL0001 Z1 01841 Heavy chain
EIQLQQSGAELGRPGSSVKLSCKTSGYTFTNFYITWLKQRPGQGLEWIGFIYPGNGYTAYNE
KFQGEATLTSDTSSSTAYMHLRSLTSEDSAIYFCARLGRNEVDYWGQGTTLTVSSAKTTPPS
VYPLAPGSAAQTNSMVTLGCLVKGYFPEPVTVTWNSGSLSSGVHTFPAVLQSDLYTLSSSVT
VPSSTWPSETVTCNVAHPASSTKVDKKIVPRDCHHHHHH (SEQ ID NO: 8)

FIG. 5

>CL0001 Z1 01321 Light chain (DNA)
GACATCGTTATGTCTCAGTCTCCATCCTCCCTAGCTGTGTCAGTTGGAGAGACGGTTACTAT
GAGCTGCAAGTCCAGTCAGACCCTTTTATATAGTAGCAATCAAAAGAATTACTTGGCCTGGT
ACCAGCAGAAACCAGGACAGTCTCCTAAATTGCTGATTTACTGGGCATCCACTAGGGAATCT
GGGGTCCCAGATCGCTTCACAGGCAGTGGATCTGGGACAGATTTCACTCTCACCATCAGCAG
TGTGAAGGCTGAAGACCTGGCAGTTTATTACTGTCAGCAATATTATGACTATCCGCTCACGT
TCGGTGCTGGGACCAAGCTGGAGCTGAAACGGGCTGATGCTGCACCAACTGTATCCATCTTC
CCACCATCCAGTGAGCAGTTAACATCTGGAGGTGCCTCAGTCGTGTGCTTCTTGAACAACTT
CTACCCCAAAGACATCAATGTCAAGTGGAAGATTGATGGCAGTGAACGACAAAATGGCGTCC
TGAACAGTTGGACTGATCAGGACAGCAAAGACAGCACCTACAGCATGAGCAGCACCCTCACG
TTGACCAAGGACGAGTATGAACGACATAACAGCTATACCTGTGAGGCCACTCACAAGACATC
AACTTCACCCATTGTCAAGAGCTTCAACAGGAATGAGTCT    (SEQ ID NO: 9)

>CL0001 Z1 01321 Heavy chain (DNA)
GACGTGCAGGTGGTGGAGTCTGGGGGAGGCTTAGTGAAGCCTGGAGGGTCCCTGAAACTCTC
CTGTGCAGTCTCTGGATTCACTTTCAGTAGTTATCACATGTCTTGGGTTCGCCAGACTCCGG
CGAAGAGGCTGGAGTGGGTCGCAACCATTAGTGGTGGTGGTGGTAACACCTACTATCCAGAC
AGTGTGAAGGGCCGATTCACCATCTCCAGAGACAATGCCAAGAACACCCTGTTCCTGCAAAT
GAGCAGTCTGAGGTCTGAGGACACGGCCTTGTATTACTGTGCAAGACATGAGGGTCCTTACT
ACTCCTTCGATGTCTGGGGCACAGGGACCACGGTCACCGTCTCTTCAGCCAAAACGACACCC
CCATCTGTCTATCCACTGGCCCCTGGATCTGCTGCCCAAACTAACTCCATGGTGACCCTGGG
ATGCCTGGTCAAGGGCTATTTCCCTGAGCCAGTGACAGTGACCTGGAACTCTGGATCCCTGT
CCAGCGGTGTGCACACCTTCCCAGCTGTCCTGCAGTCTGACCTCTACACTCTGAGCAGCTCA
GTGACTGTCCCCTCCAGCACCTGGCCCAGCGAGACCGTCACCTGCAACGTTGCCCACCCGGC
CAGCAGCACCAAGGTGGACAAGAAAATTGTGCCCAGGGATTGTCATCATCACCATCACCATC
AC    (SEQ ID NO: 11)

>CL0001 Z1 01321 Light chain
DIVMSQSPSSLAVSVGETVTMSCKSSQTLLYSSNQKNYLAWYQQKPGQSPKLLIYWASTRES
GVPDRFTGSGSGTDFTLTISSVKAEDLAVYYCQQYYDYPLTFGAGTKLELKRADAAPTVSIF
PPSSEQLTSGGASVVCFLNNFYPKDINVKWKIDGSERQNGVLNSWTDQDSKDSTYSMSSTLT
LTKDEYERHNSYTCEATHKTSTSPIVKSFNRNES    (SEQ ID NO: 10)

>CL0001 Z1 01321 Heavy chain
DVQVVESGGGLVKPGGSLKLSCAVSGFTFSSYHMSWVRQTPAKRLEWVATISGGGGNTYYPD
SVKGRFTISRDNAKNTLFLQMSSLRSEDTALYYCARHEGPYYSFDVWGTGTTVTVSSAKTTP
PSVYPLAPGSAAQTNSMVTLGCLVKGYFPEPVTVTWNSGSLSSGVHTFPAVLQSDLYTLSSS
VTVPSSTWPSETVTCNVAHPASSTKVDKKIVPRDCHHHHHH    (SEQ ID NO: 12)

FIG. 6

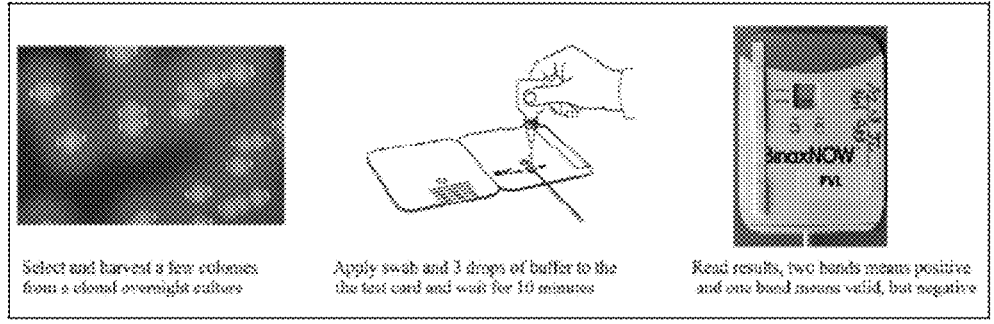

FIG. 7

| ISOLATE | STRAIN COLLECTION | STRAIN AFFILIATION | CATEGORY ACCORDING TO ANTIBODY ARRAY MEASUREMENTS | LATERAL FLOW TEST INTERPR. |
|---|---|---|---|---|
| 05V1343 | A20 | CC121-MSSA [PVL+] | HIGH LEVEL (.4,500 NG/ML) | POSITIVE/VALID |
| 06V15104 | X54 | CC22-MSSA [PVL+] | HIGH LEVEL (.4,500 NG/ML) | POSITIVE/VALID |
| AUSTR-03-16790 | Z112 | ST93-MRSA-IV [PVL+], Queensland Clone | HIGH LEVEL (.4,500 NG/ML) | POSITIVE/VALID |
| AUSTR-06-RBH-14 | Z492 | ST93-MRSA-IV [PVL+], Queensland Clone | HIGH LEVEL (.4,500 NG/ML) | POSITIVE/VALID |
| AUSTR-9529120L | Z487 | ST93-MSSA [PVL+] | HIGH LEVEL (.4,500 NG/ML) | POSITIVE/VALID |
| USA300-FPR3757 | Z330 | ST8-MRSA-IV, USA300 | HIGH LEVEL (.4,500 NG/ML) | POSITIVE/VALID |
| 05V08535 | O36 | CC96/154-MSSA [PVL+] | LOW LEVEL (<450 ng/mL) | POSITIVE/VALID |
| 05V12517 | A52 | CC5-MSSA [PVL+] | LOW LEVEL (<450 ng/mL) | POSITIVE/VALID |
| 08V10386 | X120 | CC30-MSSA [PVL+] | LOW LEVEL (<450 ng/mL) | POSITIVE/VALID |
| 08V34589 | A124 | CC22-MSSA [PVL+] | LOW LEVEL (<450 ng/mL) | POSITIVE/VALID |
| ATCC25923-Saarbrücken | R67 | CC30-MSSA [PVL+] | LOW LEVEL (<450 ng/mL) | POSITIVE/VALID |
| SARI-MRSA-0723 | Z362 | ST22-MRSA-IV [PVL+] | LOW LEVEL (<450 ng/mL) | POSITIVE/VALID |
| JENA-FLI-04-TGD-1787-816 | V571 | CC133-MSSA | BOVINE LEUKOCIDIN (lukM/lukF-PV-P83) | POSITIVE/VALID |
| JENA-FLI-KS-01-22 | V572 | CC151-MSSA | BOVINE LEUKOCIDIN (lukM/lukF-PV-P83) | POSITIVE/VALID |
| JENA-FLI-KS-02-141 | V573 | CC151-MSSA | BOVINE LEUKOCIDIN (lukM/lukF-PV-P83) | POSITIVE/VALID |
| JENA-FLI-KS-05-159 | V574 | CC479-MSSA | BOVINE LEUKOCIDIN (lukM/lukF-PV-P83) | POSITIVE/VALID |
| JENA-FLI-KS-06-234 | V575 | CC479-MSSA | BOVINE LEUKOCIDIN (lukM/lukF-PV-P83) | POSITIVE/VALID |
| JENA-FLI-Ziege-16B | V136 | CC133-MSSA | BOVINE LEUKOCIDIN (lukM/lukF-PV-P83) | POSITIVE/VALID |
| COL | R11 | CC8-MRSA-I | PVL-NEGATIVES | NEGATIVE/VALID |
| MSSA476 | R20 | CC1-MSSA | PVL-NEGATIVES | NEGATIVE/VALID |
| Mu50 | R4 | CC5-MRSA-II | PVL-NEGATIVES | NEGATIVE/VALID |
| N315 | R17 | CC5-MRSA-II | PVL-NEGATIVES | NEGATIVE/VALID |
| NCTC8325 | R15 | CC8-MSSA | PVL-NEGATIVES | FALSE POSITIVE/VALID |
| ATCC35984/NARSA 101 | R21 | *Staph. epidermis!* | PVL-NEGATIVES | NEGATIVE/VALID |

FIG. 8A

| ISOLATE | STRAIN COLLECTION | STRAIN AFFILIATION | CATEGORY ACCORDING TO ANTIBODY ARRAY MEASUREMENTS | LATERAL FLOW TEST INTERP. |
|---|---|---|---|---|
| 05V08535 | O36 | CC96/154-MSSA [PVL+] | LOW LEVEL (<450 ng/mL) | POSITIVE/VALID |
| 08V10386 | X120 | CC30-MSSA [PVL+] | LOW LEVEL (<450 ng/mL) | POSITIVE/VALID |
| AUSTR-03-16790 | Z112 | ST93-MRSA-IV [PVL+], Queensland Clone | HIGH LEVEL (>4,500 ng/mL) | POSITIVE/VALID |
| USA300-FPR3757 | Z330 | ST8-MRSA-IV, USA300 | HIGH LEVEL (>4,500 ng/mL) | POSITIVE/VALID |
| JENA-FLI-ZIEGE-16B | V136 | CC133-MSSA | BOVINE LEUKOCIDIN (lukM/lukF-PV-P83) | POSITIVE/VALID |
| JENA-FLI-KS-01-22 | V572 | CC151-MSSA | BOVINE LEUKOCIDIN (lukM/lukF-PV-P83) | POSITIVE/VALID |
| COL | R11 | CC8-MRSA-I | PVL NEGATIVES | NEGATIVE/VALID |
| NCTC 8325 | R13 | CC8-MSSA | PVL NEGATIVES | NEGATIVE/VALID |
| NCTC 8325 | R15 | CC8-MSSA | PVL NEGATIVES | NEGATIVE/VALID |

FIG. 8B

| Isolate/strain | Strain affiliation | High/low level producer | Culture on | Lat. Flow test |
|---|---|---|---|---|
| USA300-FPR3757_Z330 | ST8-MRSA-IV USA300 | HIGH LEVEL (>4,500 ng/mL) | Agar | POSITIVE/VALID |
| | | | Mueller Hinton | POSITIVE/VALID |
| | | | MRSA ID (BioMer) | POSITIVE/VALID |
| | | | Columbia Blood | POSITIVE/VALID |
| | | | Mueller Hinton with Blood | POSITIVE/VALID |
| | | | C.A.P. | POSITIVE/VALID |
| | | | "Chocolate" | POSITIVE/VALID |
| SARI-MRSA-0723_Z362 | ST22-MRSA-IV [PVL+] | LOW LEVEL (<450 ng/mL) | Agar | POSITIVE/VALID |
| | | | Mueller Hinton | POSITIVE/VALID |
| | | | MRSA ID (Bio Mer) | POSITIVE/VALID |
| | | | Columbia Blood | POSITIVE/VALID |
| | | | Mueller Hinton with Blood | POSITIVE/VALID |
| | | | C.A.P. | POSITIVE/VALID |
| | | | "Chocolate" | POSITIVE/VALID |

FIG. 9

| Isolate/strain | Strain affiliation | High/low level producer | Culture on | Lat. Flow test |
|---|---|---|---|---|
| AUSTR-03-167900_Z112 | ST93-MRSA-IV [PVL+], Queensland Clone | HIGH LEVEL (>4,500 ng/mL) | Glucose | POSITIVE/VALID |
| | | | Brain Heart | POSITIVE/VALID |
| 08V10386_X120 | CC30-MSSA [PVL+] | LOW LEVEL (<450 ng/mL) | Glucose | POSITIVE/VALID |
| | | | Brain Heart | POSITIVE/VALID |
| Mu50 | CC5-MRSA-II | NEGATIVE | Glucose | NEGATIVE/VALID |
| | | | Brain Heart | NEGATIVE/VALID |

FIG. 10

| | |
|---|---|
| TRUE POSITIVE | 301 |
| FALSE NEGATIVE | 1 |
| FALSE NEGATIVE | 5 |
| TRUE NEGATIVE | 293 |
| SENSITIVITY<br>TP / (TP + FN) | 99.7% |
| SPECIFITY<br>TN / (FP + TN) | 98.93% |
| PPV<br>TN / (TP + FP) | 98.4% |
| NPV<br>TN / (FN + TN) | 99.7% |

FIG. 11

Positive Isolates Tested:

➢ 297 isolates and five reference strains MW2-USA-400, USA300-FPR3757, ATCC25923, Queensland caMRSA (ST93-MRSA-IV), Bengal Bay caMRSA (ST772-MRSA-V0 were PVL positive.

➢ By array hybridizations, they were assigned to 21 different clonal complexes, CC1 (including ST772), CC5,CC8 (including ST72), CC15, CC22, CC25, CC30, CC45, CC49, CC59,CC80, CC88, CC93,CC96, CC121, CC152, CC188, CC398 and three unidentified lineages.

➢ The most frequently isolated PVL-positive lineages were:
  • CC8 (46 isolates including MSSA from Trinidada & Tobago as well as "USA300" from various regions)
  • CC30 (46 isolates MSSA and MRSA with SCC*mec* IV elements).
  • CC93 (42 isolates MSSA and ST93-MRSA-IV, Queensland caMRSA clone, almost exclusively from Australia)

➢ Assay also detects *lukM lukF-p83* (in animal strains CC133, CC151, CC479)

FIG. 12A

Negative Isolates Tested:

- 287 PVL-negative test isolates and seven reference strains (Sanger MSSA476, Mu50 and N315, NCTC8325, COL. West Australian (WA) MRSA-8 (ST75-MRSA-IV) and WA-MRSA-59 (a CC12-MRSA)

- Assigned to 31 different clonal complexes: CC1, CC5, CC6, CC7, CC8 (including ST72 and ST239), CC9 (ST834), CC12, CC15, CC20, CC22, CC25, CC30 (including ST34), CC45, CC50, CC59, CC75, CC80, CC88, CC96, CC97, CC101, CC121, CC140, CC188, CC398, CC425, CC509, CC707 AND CC1021 and one unknown

FIG. 12B

FIG. 13: Strains tested, their geographic origins and test results. False results in lateral flow tests are marked with "(!)"

| CC | STRAIN | Total Number | PVL-positive in lateral flow assay | PVL-negative in lateral flow assay | Australia | Germany | Saudi Arabia | Spain | Sweden | Trinidad & Tobago | Uganda | United Kingdom - London | United Kingdom - Bristol | REFERENCE Strains |
|---|---|---|---|---|---|---|---|---|---|---|---|---|---|---|
| CC1 | CC1-MSSA | 7 | - | 7 | | | | | 3 | 1 | 2 | 1 | | |
| CC1 | CC1-MSSA [PVL+] | 6 | 6 | - | 1 | 1 | | | 2 | | | | 1 | 1 |
| CC1 | CC1-MSSA-SCCfus | 8 | - | 8 | 2 | | 1 | 1 | | | | 2 | 1 | |
| CC1 | CC1-MSSA-SCCfus [PVL+] | 7 | 7 | - | 4 | | | | | | | 3 | | |
| CC1 | CC1-MRSA-IV, WA-MRSA-1/57 | 1 | - | 1 | | | | | | | | 1 | | |
| CC1 | CC1-MRSA-IV [PVL+], USA400 | 3 | 3 | - | 1 | | | | | | | | 1 | 1 |
| CC1 | CC1-MRSA-IV & SCCfus, WA-1/45 | 1 | - | 1 | | | 1 | | | | | | | |
| CC1 ST573/772 | ST573\|772-MSSA [PVL+] | 2 | 2 | - | 2 | | | | | | | | | |
| CC1 ST573/772 | ST772-MRSA-V [PVL+], Bengal Bay clone/WA-60 | 4 | 4 | - | | | | 1 | | | | 2 | 1 | 1 |
| CC5 | CC5-MSSA | 10 | - | 10 | | | | | 6 | | 2 | | | |
| CC5 | CC5-MSSA [PVL+] | 8 | 8 | - | | 1 | | | 1 | 5 | | | | 2 |
| CC5 | CC5-MRSA-II, UK-3/Rhine-Hesse/New York Japan | 3 | - | 3 | | 1 | | | | | | | | |
| CC5 | CC5-MRSA-IV, Pediatric clone | 1 | - | 1 | | | | | | | 1 | | | |
| CC5 | CC5-MRSA-IV [edinA+], WA-65 | 1 | - | 1 | 1 | | | | | | | | | |
| CC5 | QC5-MRSA-IV, Pediatric clone [PVL+] | 5 | 5 | - | | | 2 | | | | | 3 | | |
| CC5 | QC5-MRSA-IVvar, "Maltese clone" | 1 | - | 1 | | | 1 | | | | | | | |
| CC5 | CC5-MRSA-V [PVL+] | 1 | 1 | - | | | | | | | | 1 | | |
| CC6 | CC6-MSSA | 3 | - | 3 | | | 1 | | | 2 | | | | |
| CC7 | CC7-MSSA | 9 | - | 9 | | 1 | 1 | | 5 | 2 | | | | |
| CC7 | CC7-MRSA-IV | 1 | - | 1 | 1 | | 1 | | | | | | | |
| CC8 | CC8-MSSA | 41 | 3(!) | 38 | 2 | 6 | 1 | | 3 | 5 | 21 | 2 | | 1 |
| CC8 | CC8-MSSA [PVL+] | 23 | 23 | - | | | | 2 | 1 | 18 | | | 2 | |
| CC8 | CC8-MSSA-SCCfus | 1 | - | 1 | | | | | | | | 1 | | |
| CC8 | ST250-MRSA-I, Early/Ancestral MRSA | 1 | - | 1 | | | | | | | | | | 1 |
| CC8 | CC8-MRSA-IV, WA-62 | 2 | 2 | - | 2 | | | | | 2 | | | | |
| CC8 | ST8-MRSA-IV [PVL+/ACME+], USA300 | 10 | 10 | - | | 1 | | | | 3 | | 3 | | 1 |
| CC8 | ST8-MRSA-IV [PVL+/ACME-] | 10 | 10 | - | | | | 10 | | | | | | 1 |

FIG. 13A

| CC | STRAIN | Total Number | PVL-positive in lateral flow assay | PVL-negative in lateral flow assay | Australia | Germany | Saudi Arabia | Spain | Sweden | Trinidad & Tobago | Uganda | United Kingdom - London | United Kingdom – Bristol | REFERENCE Strains |
|---|---|---|---|---|---|---|---|---|---|---|---|---|---|---|
| CC8 (ST72) | ST72-MSSA | 13 | - | 13 | 2 | 1 | | 1 | | 7 | 2 | | | |
| | ST72-MSSA [PVL+] | 1 | 1 | - | | 1 | | | | | | 1 | | |
| CC8 (ST239) | ST239-MRSA-III, Vienna/Hungarian/Brazilian clone | 13 | - | 13 | | | 5 | | | 6 | 1 | 1 | | |
| CC9 9ST83-40 | ST834-MSSA | 2 | - | 2 | | | | | | | 2 | | | |
| | ST834-MRSA-VI | 1 | - | 1 | | | 1 | | | | | | | |
| CC12 | CC12-MSSA | 8 | - | 8 | | | | | 5 | 1 | | 2 | | |
| | CC12-MRSA, W A-59 | 1 | - | 1 | | | | | | | | | | 1 |
| CC15 | CC15-MSSA | 29 | 1(!) | 28 | 2 | 1 | 3 | 1 | 18 | 2 | 2 | | | |
| | CC15-MSSA [PVL+] | 2 | 2 | - | | 1 | | | 1 | | | | | |
| CC20 | CC20-MSSA | 3 | - | 3 | | | | | 3 | | | | | |
| CC22 | CC22-MSSA | 6 | 1(!) | 5 | | 3 | 1 | | 1 | | | 1 | | |
| | CC22-MSSA [PVL+] | 19 | 19 | - | | 2 | 2 | 5 | | | | | 10 | |
| | CC22-MSSA-SCCfus [PVL+] | 5 | 5 | - | | | 1 | | | | | | 5 | |
| | CC22-MRSA-IV, UK-EMRSA-15/Barnim EMRSA | 4 | - | 4 | 1 | 1 | 1 | | | | | 1 | | |
| | CC22-MRSA-IV [PVL+] | 5 | 5 | - | | 2 | 1 | | | | | 2 | | |

FIG. 13B

| CC | STRAIN | Total Number | PVL-positive in lateral flow assay | PVL-negative in lateral flow assay | Australia | Germany | Saudi Arabia | Spain | Sweden | Trinidad & Tobago | Uganda | United Kingdom - London | United Kingdom - Bristol | REFERENCE Strains |
|---|---|---|---|---|---|---|---|---|---|---|---|---|---|---|
| CC25 | CC25-MSSA | 10 | - | 10 | | | 3 | | | | 6 | 1 | | |
| CC25 | CC25-MSSA [PVL+] | 2 | 2 | - | 2 | | | | | | | | | |
| CC30 | CC30-MSSA | 20 | - | 20 | 1 | 8 | 3 | 6 | 7 | | | 1 | | |
| CC30 | CC30-MSSA [PVL+] | 35 | 34 | 1(!) | 3 | 4 | 4 | 1 | 4 | 10 | 1 | 4 | 2 | |
| CC30 | CC30-MRSA-IV [PVL+], Southwest Pacific clone | 11 | 11 | - | 5 | 1 | 1 | | 1 | | | 2 | | 1 |
| CC30 (ST34) | ST34-MSSA | 5 | - | 5 | 1 | | | | | | | | | |
| CC45 | CC45-MSSA | 33 | | | | | | | 3 | | | | | |
| CC45 | CC45-MSSA [PVL+] | 2 | 2 | - | 1 | | | | | | | | | |
| CC45 | CC45-MRSA-IV, Berlin EMRSA | 1 | - | 1 | | 1 | | | | | | | | |
| CC49 | ST149-MSSA [PVL+] | 1 | 1 | - | | | | | | | | | | |
| CC50 | CC50-MSSA | 3 | - | 3 | | | | | | | | | | |
| CC59 | CC59-MSSA | 1 | - | 1 | | | | | | | | | | |
| CC59 | CC59-MSSA [PVL+] | 1 | 1 | - | | | | | | | | 1 | | |
| CC59 | CC59-MRSA- V | 1 | - | 1 | | | | | | | | 1 | | |
| CC59 | CC59-MRSA-V [PVL+] | 1 | 1 | - | | | | | | | | 2 | | |
| CC59 | ST59/ST952-MRSA-V(T) [PVL+], "Taiwan clone" | 3 | 3 | - | 1 | | | | | | | | | |
| CC59 | CC59-MRSA- V&SCCfus | 2 | - | 2 | | | | | | 2 | | | | |

FIG. 13C

| CC | STRAIN | Total Number | PVL-positive in lateral flow assay | PVL-negative in lateral flow assay | Australia | Germany | Saudi Arabia | Spain | Sweden | Trinidad & Tobago | Uganda | United Kingdom - London | United Kingdom - Bristol | REFERENCE Strains |
|---|---|---|---|---|---|---|---|---|---|---|---|---|---|---|
| CC75 | MSSA, related to ST1223 | 2 | - | 2 | | | | | | 2 | | | | |
| | MSSA, related to ST1667 | 2 | - | 2 | | | 1 | | | 1 | | | | 1 |
| | ST75-MRSA-IV, WA-MRSA-8/79 | 1 | - | 1 | | | | | | | | | | |
| CC80 | CC80-MSSA [PVL+] | 5 | 5 | - | | | 1 | | 2 | | 1 | | | |
| | CC80-MRSA-IV | 2 | - | 2 | | | 2 | | | | | | | |
| | CC80-MRSA-IV [PVL+], European CA-MRSA clone | 13 | 13 | - | 1 | | 11 | | | | | | 2 | 1 |
| CC88 | CC88-MSSA. | 2 | - | 2 | 1 | | | | 1 | | | | | |
| | CC88-MSSA [PVL+] | 2 | 2 | - | | | 2 | | 2 | | | | | |
| | CC88-MRSA-IV [PVL+] | 2 | 2 | - | | 1 | | | | | | | | |
| CC93 | ST93-MSSA [PVL+] | 9 | 9 | - | 9 | | | | | | | | | |
| | ST93-MRSA-iV [PVL+], Queensland clone | 33 | 33 | - | 30 | 1 | 1 | | | | | 1 | | |
| CC96 | CC96/154-MSSA | 1 | - | 1 | | | | | | | | | | |
| | CC96/154-MSSA [PVL+] | 1 | 1 | - | | 1 | | | | | | | | |
| CC97 | CC97-MSSA | 8 | - | 8 | | | 1 | | 7 | | | | | |
| CC101 | CC101-MSSA | 3 | - | 3 | | | | 2 | 1 | 1 | | | | |
| CC121 | CC121-MSSA | 16 | - | 16 | | 8 | | 4 | 8 | 4 | | 1 | | |
| | CC121-MSSA [PVL+] | 50 | 50 | - | 15 | | | | 3 | | 17 | 2 | | |
| CC140 | CC140-MRSA-IV | 2 | - | 2 | | | | | | | 2 | | 1 | |

FIG. 13D

| CC | STRAIN | Total Number | PVL-positive in lateral flow assay | PVL-negative in lateral flow assay | Australia | Germany | Saudi Arabia | Spain | Sweden | Trinidad & Tobago | Uganda | United Kingdom - London | United Kingdom – Bristol | REFERENCE Strains |
|---|---|---|---|---|---|---|---|---|---|---|---|---|---|---|
| CC152 | CC152-MSSA [PVL+] | 8 | 8 | - | | | | 2 | 1 | 2 | | 1 | 2 | |
| CC152 | CC152-MRSA-V [PVL+] | 1 | 1 | - | | 1 | | | | | | | | |
| CC188 | CC188-MSSA | 6 | - | 6 | 1 | | | 1 | 2 | 2 | | | | |
| CC188 | CC188-MSSA [PVL+] | 2 | 2 | - | 1 | | | 1 | | | | | | |
| CC398 | CC398-MSSA | 1 | - | 1 | | 1 | | | | | | | | |
| CC398 | CC398-MSSA [PVL+] | 1 | 1 | - | | 1 | | | | | | | | |
| CC398 (ST391/813) | ST291/813-MSSA | 1 | - | 1 | | | 1 | | | | | | | |
| CC398 (ST391/813) | ST291/813-MRSA [PVL+] | 1 | 1 | - | | | 1 | | | | | | | |
| CC425 | ST425-MRSA-XI | 1 | - | 1 | | | 1 | | | | | | | |
| CC509 | CC509-MSSA | 1 | - | 1 | | | | | | | | 1 | | |
| CC707 | ST707-MSSA | 1 | - | 1 | | | | | 1 | | | | | |
| CC1021 | CC1021-MSSA | 1 | - | 1 | | | 1 | | | | | | | |
| CC1290 | CC1290/ST2481-MSSA | 1 | - | 1 | | | | 1 | | | | | | |
| ST2479 | ST2479-MSSA [PVL+] | 1 | 1 | - | | | | | 1 | | | | | |
| ST2482 | ST2482-MSSA [PVL+] | 4 | 4 | - | | | 3 | | | | | | | |
| Unidentified | agr IV/capsule 5 MSSA | 1 | - | 1 | | | | | | | 1 | | | |

FIG. 13E

| Country (total number of isolates) | PVL-negative MSSA | PVL-negative MRSA | PVL-positive MSSA | PVL-negative MRSA |
|---|---|---|---|---|
| Australia (n=90) | 14 (15.6%) | 2 (2.2%) | 37 (41.1%) | 37 (41.1%) |
| Germany (n=50) | 26 (52.0%) | 4 (80%) | 17 (34.0%) | 3 (6.0%) |
| Saudi Arabia (n=53) | 21 (39.6%) | 8 (15.1%) | 11 (20.8%) | 13 (24.5%) |
| Spain (n=44) | 11 (25.0%) | 0 (0%) | 23 (52.3%) | 10 (22.7%) |
| Sweden (n=114) | 95 (83.3%) | 0 (0%) | 19 (16.7%) | 0 (0%) |
| Trinidad & Tobago (n=80) | 32 (40.0%) | 8 (10.0%) | 35 (43.8%) | 5 (6.2%) |
| Uganda (n=62) | 39 (62.9%) | 4 (6.5%) | 19 (30.6%) | 0 (0%) |

FIG. 14

DEVICES AND METHODS FOR DETECTION OF PANTON-VALENTINE LEUKOCIDIN (PVL)

CROSS-REFERENCE TO RELATED APPLICATIONS

This application is a 35 USC §371 National Stage application of International Application No. PCT/US2012/064535 filed Nov. 9, 2012, which claims the benefit under 35 USC §119(e) to U.S. Application Ser. No. 61/714,649 filed Oct. 16, 2012, U.S. Application Ser. No. 61/617,974 filed Mar. 30, 2012, U.S. Application Ser. No. 61/561,767 filed Nov. 18, 2011 and U.S. Application Ser. No. 61/558,848 filed Nov. 11, 2011. The disclosure of each of the prior applications is considered part of and is incorporated by reference in the disclosure of this application.

BACKGROUND OF THE INVENTION

1. Field of the Invention

The present invention relates to devices and methods for the detection of a bacterial toxin in a biological sample. In particular, the invention relates to a lateral flow assay for identifying the presence of biomolecules produced by *Staphylococcus aureus* isolates, such as Panton-Valentine Leukocidin (PVL) and PBP2a.

2. Background Information

The following Background Information is intended to aid the reader in understanding the invention and is not admitted to be prior art.

*Staphylococcus aureus* is a clinically-relevant gram-positive coccus. About 20-30% of a healthy human population carries *S. aureus* on mucous membranes. *S. aureus* can cause a wide range of diseases, including sepsis, toxic shock, pneumonia, skin and soft tissue infections, and infection of bones and synthetic implants. *S. aureus* has also been detected in a wide range of animals.

Methicillin-resistant *Staphylococcus aureus* (MRSA) is *S. aureus* that harbor an alternate penicillin-binding protein, known as PBP2a, encoded by the gene mecA and different alleles thereof. As the name implies, MRSA can be detected by the observation of *S. aureus* growth in presence of methicillin, as well as other beta-lactam antibiotics such as penicillins, cephalosporins and carbapenems.

Because of limited treatment options, MRSA is a significant cause of morbidity and mortality of hospital patients, and poses a challenge to infection control and public health. Due to the need for expensive second-line drugs and quarantine measures, MRSA causes considerable costs to healthcare providers. There are an estimated 53 million MRSA carriers in the world and 2.5 million MRSA carriers in the United States.

The Panton-Valentine leukocidin (PVL) toxin is a phage-borne virulence factor of *Staphylococcus aureus*. It is a clinically-important phage borne virulence factor in *S. aureus* and MRSA. PVL is encoded by two adjacent and co-expressed genes, lukS-PV and lukF-PV (lukS-PV, lukF-PV, GenBank BA000033.2:MW1378 and MW1379). A T-cell epitope of lukS-PV capable of eliciting strong proliferation of $L_sT$ cells has been recently characterized: $N_{169}$ YISEVERQNSKS-VQWGIKANSFIT$_{193}$ (Brown, et al., *Open J. Immunol.*, 2(3): 111-115 (2012)). Polymers of these molecules form pores in human leukocyte membranes leading to cell death and cytokine release. Alternatively, low concentrations may induce apoptosis in granulocytes.

PVL is related to gamma-hemolysin (lukF/S-hlg) and to other leukocidins (lukE/D, lukM/lukF-P83 in *S. aureus* and lukF/S-int in *S. intermedius/pseudintermedius*). PVL is structurally, and in terms of sequence similarities, related to other leukocidins, such as lukE/D, lukM/lukF-P83 in *S. aureus* and lukF/S-int in *S. intermedius/pseudintermedius*, and to the hlgA/lukF/S-hlg gamma-hemolysin/leukocidin locus.

As discussed above, PVL is toxic for human leukocytes because it forms polymeric pores in the cell membranes of white blood cells. Leukocyte death results in cytokine release and attracts new white blood cells. PVL genes are phage-borne and mobile; they can be found in very diverse clonal complexes (e.g., CC1, 5, 8, 15, 22, 25, 30, 45, 59, 72, 80, 88, 93, 96/154, 121, 188, 398). So far, PVL is restricted to *S. aureus* strains isolated from humans. *S. aureus* from ruminants (e.g., cattle, goats and sheep) have another specific leukocidin, encoded by the genes lukM and lukF-P83 (e.g., in CC479, 151, 133, 97, 30, 20).

PVL is frequently detected in *S. aureus* isolates from skin and soft tissue infections (SSTI) as is associated with chronic/recurrent infections such as furunculosis, especially in young and previously healthy adults. PVL-positive *S. aureus* can also cause more severe diseases such as necrotizing pneumonia. This condition is occasionally a complication of other respiratory tract infections such as influenza and its fatality rate can be as high as 40%. In contrast, PVL is rarely isolated in *S. aureus* from healthy carriers or from isolates associated with other types of infections, such as bacteremia.

Although PVL was described in the 1930s, its existence as a potent leukotoxic toxin produced by some *S. aureus* strains was postulated already in the late $19^{th}$ century (28). In the 1940s and 1960s, worldwide outbreaks of PVL-positive, methicillin-susceptible *S. aureus* were observed, and by the late 1990s, PVL-positive community acquired MRSA (caMRSA) had emerged.

Many clinical conditions can be related to PVL, including skin and soft tissue infections, abscesses, furunculosis (boils), and mastitis. These conditions range from minor infections to life-threatening conditions, such as necrotizing fasciitis. PVL-associated infections tend to be chronic or recurring. *S. aureus* is also an occasional cause of pneumonia, often as a superinfection or a complication of influenza. Necrotizing pneumonia, the most serious form of pneumonia, is commonly associated with PVL, and it is often fatal.

PVL is extremely rare among *S. aureus* isolates from healthy carriers or from implant-associated infections. PVL is common among isolates from infections such as abscesses or furuncles. Because of the tendency to cause chronic, recurrent or particularly severe infections, PVL-positive *S. aureus* strains warrant different, more aggressive treatment than "normal" *S. aureus* strains. In Great Britain, this is already officially recommended by a guideline by the Health Protection Agency.

To date, PVL detection is primarily achieved using a molecular method that is essentially limited to reference centers and specialized laboratories with equipment and experience to perform such assays. Current methods for detecting PVL and PBP2a include polymerase chain reaction (PCR) for the identification of PVL and PBP2a genes. PCR can be performed only in specialized laboratories with dedicated hardware and trained personnel, and requires sample preparation. Patients who present to family physicians and primary care centers may not have ready access to such laboratory facilities. These cases remain undiagnosed and thus possibly not adequately treated, resulting in greater health risks to the patient and potential economic consequences to doctors and hospitals. Other methods for the identification of PVL producing *S. aureus* and methicillin-resistant *S. aureus*, such as those disclosed in US 2010/0129839, require pretreatment (i.e., heating) of the biological sample to denature the PVL, in addition to more time and work consuming immunological assays such as ELISA.

Therefore, a continuing need exists for methods and devices for rapid detection of PVL, PBP2a and *S. aureus* Protein A (SPA) with minimal sample processing, while ensuring accurate and reliable results. A simple, rapid assay could facilitate diagnosis of PVL-associated disease in primary and secondary health care facilities as well as determine whether the strain in methicillin-resistant. Rapid assays save time, as results from reference laboratories often take several days or weeks. A test which distinguishes PVL-positive MRSA from PVL-negative MRSA strains may ultimately result in greater treatment benefits to the patient and assist in preventing the spread of the former within hospital settings. Further, a test which distinguishes PBP2a-positive MRSA from PBP2a-negative MRSA strains may ultimately result in greater treatment benefits to the patient and assist in preventing the spread of the former within hospital settings.

SUMMARY OF THE INVENTION

The present invention provides a rapid lateral flow assay that detects a biomolecule, such as PVL, PBP2a, and SPA in a biological sample. The assay comprises recombinant antibodies raised against *S. aureus* PVL, PBP2a and SPA using phage display technology.

In embodiments, the biological sample is a culture, a liquid culture, a wound swab, a nasal swab, or, in veterinary medicine, a wound or udder swab. In embodiments, primary cultures are collected from patients with infections, for example furunculosis and abscesses, potentially caused by a variety of pathogens.

The summary of the invention described above is not limiting and other features and advantages of the invention will be apparent from the following detailed description, as well as from the claims.

BRIEF DESCRIPTION OF THE DRAWINGS

FIG. 1A is a tabular representation depicting data from toxin antibody assays in embodiments of the invention, showing PVL concentrations produced in vitro by representative strains.

FIG. 2 is a tabular representation depicting data from toxin antibody assays in embodiments of the invention in order to show that different strains producing different toxin concentrations are recognized.

FIG. 3 is a tabular representation depicting data from toxin antibody assays in embodiments of the invention. A matrix is depicted for an array-based determination of optimal combinations of antibodies. 0, no reactivity; (+) to +++, weak to strong reactivities, based on multiple experiments under varying conditions.

FIG. 4 is a graphical representation depicting DNA and protein sequence information for an antibody in one embodiment of the invention (PVL-1401).

FIG. 5 is a graphical representation depicting DNA and protein sequence information for an antibody in one embodiment of the invention (PVL-1841).

FIG. 6 is a graphical representation depicting DNA and protein sequence information for an antibody in one embodiment of the invention (PVL-1321).

FIG. 7 is a graphical representation depicting an assay procedure using a Binax card format in embodiments of the invention.

FIG. 8A is a tabular representation depicting data from toxin antibody assays in embodiments of the invention in order to show that different strains producing different toxin concentrations are recognized.

FIG. 8B is a tabular representation depicting data from toxin antibody assays in embodiments of the invention in order to show that different strains producing different toxin concentrations are recognized.

FIG. 9 is a tabular representation depicting data from toxin antibody assays in embodiments of the invention in order to show that different solid growth media can be used.

FIG. 10 is a tabular representation depicting data from toxin antibody assays in embodiments of the invention in order to show that different liquid growth media can be used.

FIG. 11 is a tabular representation depicting data from toxin antibody assays in embodiments of the invention. Sensitivity, specificity, positive and negative prediction values are shown as obtained by testing 588 clinical isolates and 12 reference strains which were characterized in parallel by molecular means (DNA array).

FIG. 12 A lists strains and clonal complexes from which PLV-positive isolates were identified to develop a toxin antibody assay in embodiments of the invention.

FIG. 12 B lists strains and clonal complexes from which PLV-positive isolates were identified to develop a toxin antibody assay in embodiments of the invention.

FIGS. 13A-13E are tabular representations depicting data of the initial trial on clinical isolates from several countries.

FIG. 14 is a tabular representation depicting rates of PVL-negative MSSA, PVL-negative MRSA, PVL-positive MSSA and PVL-positive MRSA by study site.

DETAILED DESCRIPTION OF THE INVENTION

Figure 1B:
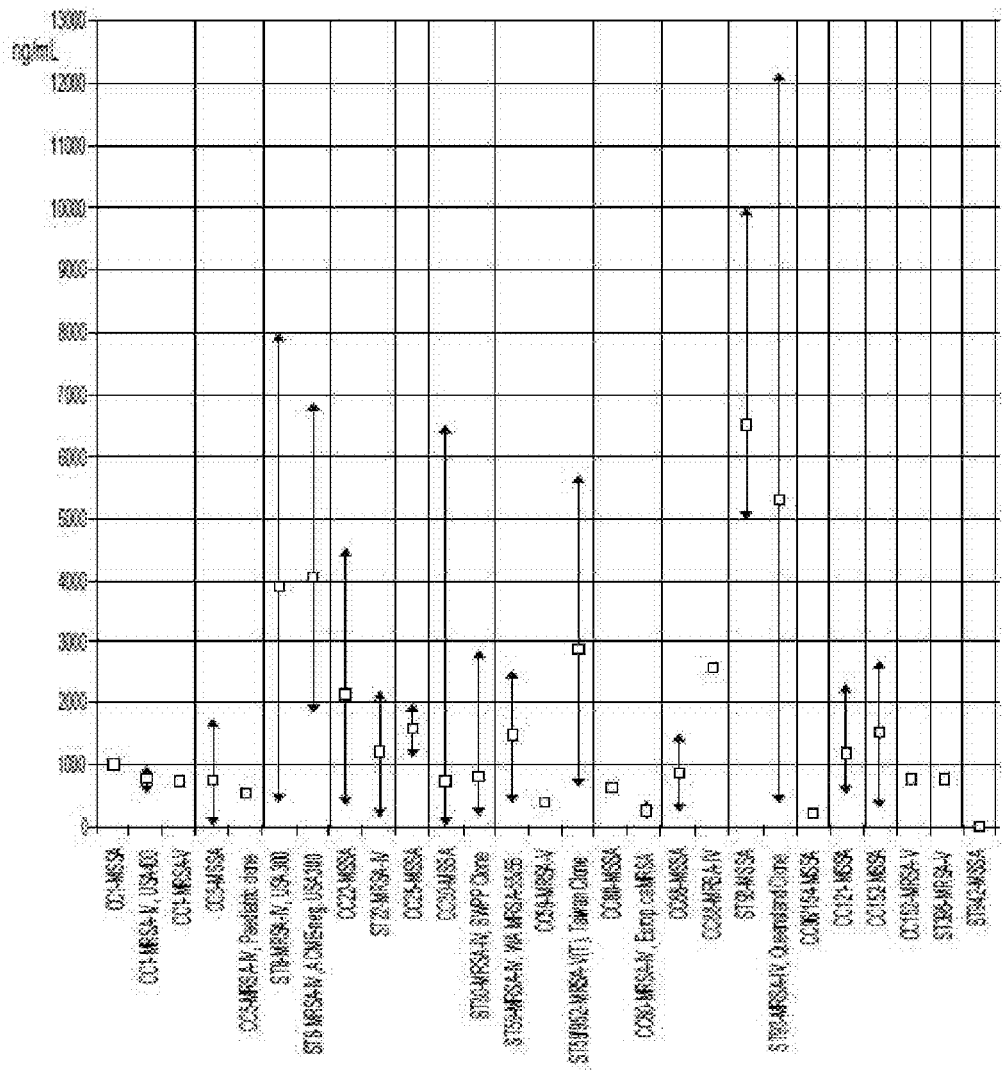
FIG. 1B is a graphical representation depicting data from toxin antibody assays in embodiments of the invention showing PVL concentrations produced in vitro by representative strains.

The present invention provides devices and methods for determining the presence or amount of an analyte in a sample. In one embodiment, the invention provides devices and methods for the detection of a bacterial biomolecules or toxin, for example *S. aureus* PVL or PBP2a, in a biological sample. In one embodiment the sample is a biological sample from a patient.

A HisTaq-PVL fusion plasmid was created using a PCR-product comprising the entire open reading frame of one of the two components of PVL, lukF-PV, from the sequenced reference strain MW2/USA400. The purified lukF-PVL fusion protein was synthesized, isolated and purified. The purified material was used as antigen for initial immunization and subsequently to produce antibodies through specific phage display technology. Native and recombinant PVL was used to characterize phage display antibodies using different technologies. A similar approach was utilized to develop antibodies to PBP2a and SPA.

The phage display antibodies were characterized initially by ELISA and spotted in different dilutions in microtiter tube/strip-mounted protein microarrays (proprietary Array-Tube™ (AT) or ArrayStrip™ (AS) platforms as developed by Alere Technologies GmbH). All possible combinations of capture and detection antibodies were tested with microarrays in order to find the most specific and most sensitive antibody pairing under a set of specific conditions using recombinant and native toxin preparations of known concentrations. Thus, each possible combination of these antibodies was tested, and pairs that detected PVL, SPA or PBP2a with highest sensitivity and specificity were identified.

Phage display antibodies generated against recombinant biomolecules were screened for reactivity not only against the HisTaq fusion protein but also against the native form of the biomolecule. Results from a microarray assay demonstrated that the recombinant antibodies recognized the native biomolecule. These antibodies were then used to develop a rapid lateral flow assay to detect biomolecules including PVL, SPA and PBP2a. By serial toxin dilutions, the detection limit of the lateral flow was shown to be in the order of magnitude around 1 ng/mL (see below). Antibodies immobilized on microarrays were used to assess the biomolecule production by clinical isolates of S. aureus. Generally, there was a correlation between clonal complex affiliation and exotoxin yield under identical culture conditions.

Collections of clinical isolates of USA300 (ST8 MRSA-IV, with a mean of about 4,000 ng/mL PVL, F-component), the Queensland Clone (ST93-MRSA-IV, about 5,000 ng/mL), ST93-MSSA (ca. 6,500 ng/mL) and ST59-MRSA-VT (about 3,000 ng/mL) yielded on average clearly more PVL than other PVL-positive MRSA or MSSA strains such as, for example, ST80-MRSA-IV (ca. 250 ng/mL), and CC5-MSSA (ca. 750 ng/mL). These experiments proved that any strain yet tested yields concentrations of PVL which are clearly above the detection limit of the selected antibody combinations.

In one embodiment, the antibodies used in a test device are recombinant phage display antibodies specific for PVL, SPA or PBP2a. In embodiments, the antibodies used in a test device are one or more of the following antibody clones: PVL-1031, PVL-1061, PVL-1101, PVL-1321, PVL-1401, PVL-1451, PVL-1631, PVL-1711, PVL-1771, PVL-1841, PVL-1881, PBP2a-1631, PBP2a-1721, PBP2a-1941, PBP2a-6G10, PBP2a-17A10, PBP2a-17C8, PBP2a-19B1, PBP2a-8A5, PBP2a-9C6, PBP2a-pc-2.1, PBP2a-pc-2.2, SPA-A135, and SPA-4412.

In embodiments, antibody pairs include antibody clone PVL-1841, which may be conjugated to a gold particle, and antibody clone PVL-1401, which can be immobilized, e.g., on a nitrocellulose membrane as a capture antibody. In other embodiments, antibody pairs include antibody clone PVL-1841, which may be conjugated to a gold particle, and antibody clone PVL-1321 and antibody clone PVL-1401 as capture antibodies immobilized, e.g., on a nitrocellulose membrane. Antibody clone PVL-1321 detects human PVL, whereas antibody clone PVL-1401 detects human PVL and the bovine variant (lukF-P83) that is involved in the pathogenesis of bovine mastitis.

In one embodiment, an assay can be used to detect biomolecules from cultures of S. aureus under the conditions of a basic microbiological laboratory. In some embodiments, performing the assay uses basic equipment, e.g., loops, culture media, and incubators, and basic expertise in bacteriology and biosafety. The present invention allows for rapid detection of PVL, PBP2a and SPA, e.g., directly from overnight bacterial cultures using an assay without the use of specialized equipment, e.g., thermocyclers, without denaturisation of the biomolecule, e.g., by heating, and without expertise for molecular techniques, i.e., nucleic acid amplification.

In embodiments, swabs are obtained from patient skin and soft tissue infections (SSTI; e.g., abscesses and furunculosis) to perform an assay. Swab samples may be cultured on solid media primary cultures overnight. S. aureus colonies can be identified in the primary culture and tested for the presence of PVL, PBP2a and/or SPA. In cases of mixed cultures or contamination with skin flora, secondary cultures are obtained by isolating S. aureus using standard laboratory procedures. Biomolecules in either primary or secondary cultures is detected using an assay device, such as a lateral flow dipstick, card or cassette.

A variety of test devices may be used to detect the presence or absence of biomolecules in the biological sample. In one embodiment, the test device may be an immunoassay device, such as lateral flow test strips, which are widely available for testing a broad range of analytes. However, any suitable assay device can be used in the present invention.

In one embodiment, a folding card format assay device, such as those described in U.S. Pat. No. 5,468,648 to Howard Chandler (herein incorporated by reference in its entirety), may be used. In another embodiment, a cassette format assay device may be used. A variety of analytes can be detected or quantified by the test devices described in the present invention. The analyte may be an infectious agent.

Test strips are available in a variety of formats, such as immunoassay or chemical test format, for detecting analytes of interest in a sample. The use of reagent-impregnated test strips in specific binding assays, such as immunoassays, is well-known (see, e.g., U.S. Pat. No. 5,622,871 to May, et al., herein incorporated by reference in its entirety). Test strips can also be configured for either noncompetitive or competitive assay formats. In some formats, the test strips have a bibulous material having a sample application zone, a reagent zone, and a test result zone. The sample is applied to the sample application zone and flows into the reagent zone by capillary action. In the reagent zone, the sample dissolves and mixes with reagents necessary for detection of the analyte (if present). The sample, now carrying the reagents, continues to flow to the test results zone. Additional reagents are immobilized in the test results zone, such as a specific binding molecule for the analyte. These reagents react with and bind the analyte (if present) or one of the first reagents from the reagent zone. Labels for providing the detectable signal can be present in the reagent zone, or in a separate label zone.

Typically, in noncompetitive formats, a signal is produced if the sample contains the analyte, and no signal is produced if the analyte is not present. In competitive formats, a signal can be produced if no analyte is present and no signal if analyte is present.

In embodiments where the analyte is detected by a signal producing system, such as by one or more enzymes that specifically react with the analyte, one or more components of the signal producing system can be bound to the analyte detection zone of the test strip material in the same manner as specific binding members are bound to the test strip material, as described above. Alternatively or in addition, components of the signal producing system that are included in the sample application zone, the reagent zone, or the analyte detection zone of the test strip, or that are included throughout the test strip, may be impregnated into one or more materials of the test strip. This can be achieved either by surface application of solutions of such components or by immersion of the one or more test strip materials into solutions of such components. Following one or more applications or one or more immersions, the test strip material is dried. Alternatively or in addition, components of the signal producing system that are included in the sample application zone, the reagent zone, or the analyte detection zone of the test strip, or that are included throughout the test strip, may be applied to the surface of one or more test strip materials of the test strip as was described for labeled reagents.

In use, a sampling device, for example a swab, can be used to collect a biological sample, such as a sample from an infected wound on a patient. Once the sample is collected, it may be grown in media, or applied directly to a testing device. The biological sample may be incubated in a solid or liquid medium for a period of time before it is applied to an assay device, as further described in the examples below. The sample is applied to an assay device to determine the presence or concentration of the analyte of interest. In embodiments, the test may be used to detect the presence, absence, or concentration of S. aureus PVL alone, S. aureus PBP2a alone, SPA alone, or any combinations thereof, or further combinations including other relevant markers such as, for example, toxic shock syndrome toxin (encoded by tstl), enterotoxin A (entA or sea), enterotoxin B (entB or seb), leukocidins from S. pseuintermedius, S. intermedius, or S. delphinii, alpha toxin (hemolysin alpha, hla), or hemolysin beta (hlb). In other embodiments, the methods and devices described above can be used to detect S. aureus or its toxins in samples derived from animals. For example, S. aureus clonal complexes CC 151 and 479 predominate in various species of ruminants, including dairy cows, and they are a common cause of bovine mastitis. Apparently, most cattle strains carry leukocidin lukM/lukF-P83, which can be used as a marker for the differentiation of epidemic strains in cattle herds from accidentally transmitted human strains.

As discussed herein, the present invention provides antibodies, or functional binding fragments thereof, that specifically bind a PVL toxin. The antibodies, or antibody fragments are capable of specifically binding a biomolecule without the need of pretreating, for example, by denaturing the biomolecule. In one embodiment, an antibody, or a functional binding fragment thereof, specifically binds an expression product of one or more of the following genes: lukS-PV, lukF-PV, lukM, lukF-P83, mecA, and spa. For example, an antibody of the invention may be one with specificity for the T-cell epitope of lukS-PV: $N_{169}$YISEVERQNSKSVQWGIKANS-FIT$_{193}$ (Brown, et al., Open J. Immunol., 2(3):111-115 (2012)).

In one embodiment, the antibodies of the present invention include clones PVL-1031, PVL-1061, PVL-1101, PVL-1321, PVL-1401, PVL-1451, PVL-1631, PVL-1711, PVL-1771, PVL-1841, PVL-1881, PBP2a-1631, PBP2a-1721, PBP2a-1941, PBP2a-6G10, PBP2a-17A10, PBP2a-17C8, PBP2a-19B1, PBP2a-8A5, PBP2a-9C6, PBP2a-pc-2.1, PBP2a-pc-2.2, SPA-A135, and SPA-4412. However, one skilled in the art would understand that identical, or substantially identical antibodies may be generated by any number of methods known in the art.

In particular, antibodies having the affinities for PVL demonstrated herein may be identified by, for example, competition assays using the disclosed antibodies, especially ones shown to have a high affinity for PVL; i.e., PVL-1321, PVL-1401 and PVL-1841. Antibodies may also be those which share binding regions for PVL epitopes. In that respect, those of skill in the art will be familiar with techniques for binding region identification in antibodies including, without limitation, the modeling techniques disclosed in Whitelegg and Rees, Protein Engineering 13 (12): 819-824 (2000); Marcatili, et al. Bioinformatics, 24 (17): 1953-1954 (2008); and Sivasubramanian, et al. Proteins, 74 (2): 497-514 (2009).

As used herein, the term "antibody" is used in its broadest sense to include polyclonal and monoclonal antibodies, as well as functional binding fragments of such antibodies. An antibody useful in a method of the invention, or a functional binding fragment thereof, is characterized, for example, by having specific binding activity for an epitope of a PVL toxin.

The term "binds specifically" or "specific binding activity," when used in reference to an antibody means that an interaction of the antibody, or a functional binding fragment thereof, and a particular epitope has a dissociation constant of at least about $1\times10^{-6}$, generally at least about $1\times10^{-7}$, usually at least about $1\times10^{-8}$, and particularly at least about $1\times10^{-9}$ or $1\times10^{-10}$ or less. As such, Fab, F(ab')2, Fd and Fv fragments of an antibody that retain specific binding activity for an epitope of PVL are included within the definition of an antibody.

Further, the term "antibody" as used herein includes naturally occurring antibodies as well as non-naturally occurring antibodies, including, for example, single chain antibodies, chimeric, bifunctional and humanized antibodies, as well as antigen-binding fragments thereof.

In various embodiments, PVL, PBP2a and/or SPA is detected in combination with one or more additional analytes. For example, the methods and devices herein may be adapted to detect one or more of enterotoxin A (entA), enterotoxin B (entB), toxin shock syndrome toxin (tstl), alpha toxin, hemolysinalpha (hla), hemolysinbeta (hlb), and staphylokinase (sak).

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

Toxin Antibody Analysis

FIGS. 1A and 1B show PVL concentrations and clonal complex affiliations for a number of S. aureus strains (both MRSA and MSSA).

Example 1

Culture Parameters:

| Culture Parameters | |
| --- | --- |
| Inoculum | One bead from cryobank |
| Medium | Kato&Noda broth |
| Incubation period | 18 hours |

Previously characterized strains of PVL producing S. aureus (high and low level producers and bovine variant) were grown in Kato&Noda broth medium overnight for PVL production. Culture supernatants were tested using the lateral flow PVL assay (dipstick format). As shown in FIG. 2, there was nearly full concordance with the microarray assay results. A weak false positive result was observed for S. aureus strain NCTC 8235.

Example 2

Culture Parameters:

| Culture Parameters | |
| --- | --- |
| Inoculum | One bead from cryobank |
| Medium | Kato&Noda broth |
| Incubation period | 2 hours |

Previously characterized strains of PVL producing S. aureus (high and low level producers and bovine variant) were tested in Kato&Noda broth medium for 2 hours and assayed for PVL production using the lateral flow PVL dipstick assay. There was nearly full concordance with the microarray assay results.

Example 3

Culture Parameters:

| Culture Parameters | |
|---|---|
| Inoculum | Picked colonies from blood agar (old culture, after 48 hours in refrigerator) |
| Medium | Blood agar culture |
| Incubation period | 18-24 hours |

Previously characterized strains of PVL producing *S. aureus* (high and low level producers and bovine variant, lukM/lukF-P83) were inoculated onto blood agar plates and grown overnight. Isolated colonies were tested directly from overnight agar plates for PVL production. There was full concordance with microarray results.

Example 4

Culture Parameters:

| Culture Parameters | |
|---|---|
| Inoculum | Overnight cultures from various growth media as specified in FIG. 5 |
| Medium | Series of solid growth media (agar) |
| Incubation period | 18-24 hours |

Previously characterized strains of PVL producing *S. aureus* (PVL-positive ST8-MRSA-IV USA300 and ST22-MRSA-IV) were tested directly from overnight agar plates using different solid media for PVL production. Isolated colonies were tested directly from overnight agar plates using the lateral flow PVL assay (dipstick format). There were positive results with all solid media.

Example 5A

Culture Parameters:

| Culture Parameters | |
|---|---|
| Inoculum | One loop from cryobank |
| Medium | BioMerieux MRSA ID chromogenic agar |
| Incubation period | 18-24 hours |

Previously characterized strains of PVL producing *S. aureus* (many different clonal complexes) were tested directly from overnight agar plates using MRSA ID™ chromogenic agar (BioMerieux) for PVL production. Isolated colonies were tested directly from overnight agar plates using the lateral flow PVL assay (dipstick format). There were positive results with all clonal complexes.

Example 5B

Culture Parameters:

| Culture Parameters | |
|---|---|
| Inoculum | One loop from cryobank |
| Medium | BioMerieux MRSA ID chromogenic agar |
| Sample preparation: | One loop in A1 buffer from Staphytype |
| Incubation period | 24 hours |

Previously characterized *S. aureus* strains (many different clonal complexes) negative for PVL were tested directly from overnight agar plates using MRSA ID™ chromogenic (BioMerieux) agar for PVL production. Isolated colonies were tested directly from overnight agar plates using the lateral flow PVL assay (dipstick format). There was full concordance with microarray results using negative controls from different clonal complexes.

Example 6

Serially diluted PVL toxin from *S aureus* strain ATCC25923 (purified from supernatant of cultures in Kato&Noda broth) was used to determine the detection limit of the dipstick assay format. The antigen concentration was 10 μg/mL. Different dilutions (end concentrations) were applied and used with the lateral flow PVL assay (dipstick format) with the described protocol. As a reference, the detection limit using protein arrays (ArrayStrip™) was determined to be ~0.5 ng/mL.

| Final concentrations after adding 200 μl Reagent A |
|---|
| 33.3 ng/mL |
| 10 ng/mL |
| 1 ng/mL |
| 0.1 ng/mL |
| 0.01 ng/mL |
| 0.001 ng/mL |

The detection limit was determined to be ~1 ng/mL.

Example 7

Non-purified PVL toxin from *S. aureus* strain ATCC25923 supernatants was used to determine the detection limit of the lateral flow PVL assay (dipstick format) with the influence of all components of the Kato&Noda medium. Different dilutions (final concentrations) were applied and used with the lateral flow PVL assay (dipstick format) with the described protocol. The detection limit was determined to be ~1 ng/mL. These results in combination with example 6 demonstrate that there does not appear to be an influence of Kato&Noda broth components on the detection limit of the assay.

| PVL concentration (ArrayStrip ™ test) ~15 μg/mL Detection limit of ToxArray ™ was ~1.5 ng/mL Final concentrations in 200 μl Reagent A, diluted in 1xPBS |
|---|
| 33.3 ng/mL |
| 16.7 ng/mL |
| 3.33 ng/mL |
| 1.67 ng/mL |
| 0.33 ng/mL |
| 0.033 ng/mL |

The detection limit was determined to be ~1 ng/mL.

Example 8

Specificity of the lateral flow PVL assay was determined by testing coagulase negative Staphylococcus (CNS) strains as negative controls. A collection of CNS strains were grown overnight on Columbia blood agar and in Kato&Noda broth medium. Isolated colonies directly from the Columbia blood agar as well as the Kato&Noda supernatants were tested using the lateral flow PVL assay (dipstick format).

All CNS strains grown on Columbia blood agar tested negative on the PVL assay. When grown in Kato&Noda broth, all CNS strains belonging to species which are frequently detected in humans tested negative on the PVL assay.

Example 9

Previously characterized strains of S. aureus including a high and a low PVL producer, a strain negative for PVL and a strain (NCTC 8325) yielding a false positive result when grown in Kato&Noda broth medium were streaked onto Columbia blood agar overnight. Isolated colonies were sub-cultured overnight in Glucose broth and Brain heart infusion broth. Supernatant samples from each growth media were tested directly for PVL production using the lateral flow PVL assay (dipstick format).

The strain negative for PVL remained so with both media. The strain shown to be a false positive in Kato&Noda broth was negative for PVL in both media. The high and low PVL producer was positive with the lateral flow PVL test using both media.

Example 10

Previously characterized strains (cryo bank beads) of S. aureus, including a high and low PVL producer, were streaked onto Columbia blood agar overnight. Isolated colonies were sub-cultured overnight in Glucose broth and Glucose broth supplemented with either human blood or $Fe^{++}$. Similarly, isolated colonies were sub-cultured overnight in Schaedler liquid broth and Schaedler broth supplemented with human blood or $Fe^{++}$. Supernatant samples from each growth media were tested directly for PVL production using the lateral flow PVL assay (dipstick format). No PVL production was observed in either media plain or supplemented with $Fe^{++}$. However, the addition of human blood into either of the growth media resulted in PVL expression.

Example 11

A study was designed to determine if normal bacterial flora and secretions from nasal samples would interfere with the lateral flow PVL assay. Specifically, nasal samples were collected from S. aureus positive and negative patients using Puritan 25-3316 nasal swabs. Previously characterized S. aureus strains were spiked (~$10^5$ CFU) directly into the nasal samples. Kato&Noda liquid medium was inoculated with the swab sample and cultured overnight. The culture media was tested for PVL using the lateral flow PVL assay (dipstick format). The normal nasal flora did not appear to interfere with the PVL assay. Results from this experiment show the potential that the test can be used to screen nasal samples and these samples can be cultured and tested for PVL.

Example 12

In order to assess the potential for use under conditions of a routine laboratory, different incubation times and growth media were tested.

Using liquid media, S. aureus were grown three to 12 hours at 36° C. on a shaker using one of the following liquid growth media: glucose broth, brain heart infusion, or Kato&Noda medium. Overnight cultures were tested for PVL production using the lateral flow PVL assay (dipstick format). The testing was performed according to the protocol provided. Two hundred microliters of test reagent was pipetted into reaction tubes that contain the assay conjugate pellet. The tubes were vortexed until the assay conjugate (purple pellet) was resuspended. One hundred microliters of the overnight cultures were added to the tubes and tubes were shaken. The dipstick was inserted into the reaction tube containing the test reagent and culture sample. The result was read after ten minutes. The observation of two stripes or lines (Test and Control) was regarded as a positive result. The observation of the control line only was regarded as a negative result.

Alternatively, using solid media, S. aureus was grown overnight at 36° C. on one of the following solid growth media: plain agar, Mueller Hinton agar, MRSA ID™ chromogenic medium (BioMerieux), Columbia blood agar, Mueller Hinton agar with blood, C.A.P. agar, and "chocolate" agar. After growing overnight isolated colonies were harvested and re-suspended in 100 microliters of one of the following buffers: buffer Al (from Alere Staphytype assay), PBS, or TRIS/EDTA. Two hundred microliters of test reagent was pipetted into the reaction tubes containing the conjugate (purple pellet). The pellet was resuspended by vortexing. To the reaction tube, 100 µL of the resuspended bacteria was added and mixed by vortexing. Alternatively, a loop of colony material was harvested and dissolved directly into the reaction tube containing 200 µL of the test reagent. The dipstick is placed into the reaction tube containing the reaction reagent and test sample. The result was read after ten minutes. The observation of two stripes or lines (Test and Control) was regarded as a positive result. The observation of the control line only was regarded as a negative result. Concentrations of PVL starting from approximately 1-5 ng/mL and above were detected by this assay.

Example 13

In this example, isolates cultured from clinical conditions in which PVL might be found at a reasonable rate were examined. Isolates from the following conditions were used: cutaneous abscesses, "spider bite" lesions (especially when chronic/recurrent), furunculosis ("boils"), carbuncles, abscess-forming mastitis, cellulitis, and unusual or severe skin & soft tissue infections, such as tropical pyoderma or necrotizing fasciitis. Identification of the agent S. aureus and susceptibility tests as well as the detection of PVL genes by molecular means and the assignment to clonal complexes and strains were performed separately.

231 S. aureus clinical isolates from North America, Europe, Australia, Africa and the Middle East were tested. 123 isolates belonging to 26 distinct strains of S. aureus were PVL-positive. 108 isolates from 33 strains of S. aureus were PVL-negative.

The lateral flow PVL assay (dipstick format) yielded the results shown in Table 1 below (repeated experiments included).

TABLE 1

Results of Lateral Flow PVL Assay (Dipstick Format).

| | |
|---|---|
| True positive results | 124 |
| True negative results | 108 |
| False positive results | 2 |
| False negative results | 0 |
| Sensitivity | 100% |
| Specificity | 98.18% |
| Positive predictive value | 98.41% |
| Negative predictive value | 100% |

The lateral flow PVL assay (card format) yielded the results shown in Table 2 below (repeated experiments included).

TABLE 2

Results of Lateral Flow PVL Assay (Card Format).

| | |
|---|---|
| True positive results | 23 |
| True negative results | 48 |
| False positive results | 6 |
| False negative results | 0 |
| Sensitivity | 100% |
| Specificity | 88.89% |
| Positive predictive value | 79.31% |
| Negative predictive value | 100% |

Example 14

A study was performed involving the rapid detection of PVL in *Staphylococcus aureus* cultures by monoclonal antibodies using a lateral flow assay. The objectives of the study was to assess the lateral flow assay in detection of PVL.

As discussed herein, PVL is a phage born virulence factor of *Staphylococcus aureus*. It comprises two units (S and F components) that are encoded by two separate, although co-localized and co-expressed genes. Polymers of these molecules form pores in human leukocyte membranes leading to cell death. PVL is associated with chronic/recurrent skin and soft tissue infections (SSTI), especially in young and previously healthy adults, and necrotizing pneumonia. Because of its clinical relevance, the detection of *S. aureus* which carry PVL genes warrants aggressive therapy and infection control measures (see world wide web at hpa.org.uk/webc/HPAweb-File/HPAweb_C/1218699411960). However, PVL detection is currently essentially limited to reference centers and specialized laboratories as it is performed by molecular methods. In order to facilitate a rapid, non-molecular detection in clinical laboratories, monoclonal antibodies were raised and a lateral flow test was developed.

Over-expressed PVL, F-component, was used to generate monoclonal antibodies via phage display. Following immunization of mice, mRNA from B-cells was isolated and amplified. Resulting cDNA, specific for the antigen-binding parts of antibodies, was ligated into bacteriophages and then transformed into *E. coli*. Resulting antibodies were purified, characterized initially by ELISA and spotted in different dilutions in microtiterstrip-mounted protein microarrays. This allowed to rapidly determine the optimal combination of capture and detection antibodies. These antibodies were used to design a lateral flow test, i.e., an immunochromatographic test in which gold-labeled detection antibodies are mixed with sample material (*S. aureus* cultures) flow by capillary action towards a zone of immobilized detection antibody. In positive cases, the formation of a visible line was observed. Two differently manufactured test formats (dipstick and Binax cards) were used in parallel for optimization of handling and protocols. This test was applied to isolates of *S. aureus* from skin and soft tissue infections that in parallel were genotyped by microarray hybridization in order to determine strain and clonal complex affiliation as well as their PVL-status.

FIG. 7 depicts the test procedure for the Binax card format. For the dipstick format, the cultures are harvested with an inoculation loop and stirred in a tube containing a buffer with the labeled antibodies. Then, the dipstick is placed into the tube. The result is read after 10 minutes.

For the selection of the optimal combination of capture and labeling antibodies, four different concentrations of each antibody was spotted onto protein microarrays. These arrays were tested with recombinant PVL F-component, native PVL (in two different concentrations, from strain ATCC25923) or "bovine leukocidin" lukM/lukF-P83 from a veterinary CC705 isolate as well as with all biotin-labeled preparations of all antibodies. Based on the results, a combination of Antibody 5 and Antibody 10 was selected for establishing a lateral flow assay that can detect PVL (F component) as well as the gene product of lukF-P83.

In a first series of experiments, known strains cultured on different growth media were tested. Detectable PVL production was noted in a broth as described by Kato&Noda or by Schaedler, in Brain Heart infusion as well as in colony material harvested from Plain Agar, Mueller Hinton agar with and without blood, MRSA ID agar (BioMerieux), Columbia Blood, C.A.P. and "chocolate" agar. False negative results were occasionally observed with glucose broth as well as false positives with clonal complex CC8 strains from Kato&Noda broth or blood agar. These lateral flow tests were used to screen a total of 450 clinical isolates obtained from diagnostic specimens from SSTI. These isolates originated from Australia, Trinidad & Tobago, the United States, the UK, Germany, Sweden, Spain, Norway, Japan, Uganda and Saudi-Arabia. 258 isolates proved to be positive. They belonged to isolates belonged to 37 different strains from 20 clonal complexes. 192 PVL-negative isolates have been tested belonging to 47 different strains from 29 clonal complexes. The proportion of PVL-positive isolates among all SSTI isolates tested ranged between 10.5% (Swedish samples) and 81.4% (Australian samples).

This test allows the rapid detection of PVL under conditions of a routine bacteriological laboratory that is not able to perform molecular assays. As it utilizes pure overnight cultures from standard media (including a chromogenic agar for MRSA screening), it can easily be integrated into such a laboratory's workflow. Thus it is expected to contribute to timely therapeutic interventions in cases of PVL-associated infections, as well as assist in selecting isolates that are to be submitted for further typing in reference centers.

Example 15

Screening assays were performed to assess detection of PBP2a using PBP2a binding antibodies generated by phage display technology as discussed herein. Serially diluted PBP2a from *S aureus* strain USA300 was also used to assess detection. There were positive results with a number of clonal complexes (data not shown).

Example 16

Previously characterized strains of *S. aureus* (many different clonal complexes) were tested for PBP2a and SPA production using antibodies of the invention. There were positive results with a number of clonal complexes (data not shown).

Example 17

Previously characterized strains of S. aureus (many different clonal complexes) were tested for PVL, PBP2a and SPA production using antibodies of the invention. There were positive results with a number of clonal complexes (data not shown).

Example 18

This Example describes the development of a lateral flow test using monoclonal antibodies described herein to facilitate the rapid, non-molecular detection of PVL by routine clinical microbiology laboratories. The assay was validated against isolates grown in a variety of different culture media, and then the assay was evaluated using an international collection of S. aureus recovered from SSTI.

To develop a rapid phenotypic assay, recombinant PVL F-component was used to generate monoclonal antibodies by phage display. Spotted on protein microarrays, these antibodies were screened using different lukF preparations and detection antibodies. This led to the identification of the optimal antibody combination that was then used to establish a lateral flow assay. This test was used to detect PVL in S. aureus cultures. The detection limit of the assay with purified native and recombinant antigens was determined to be around 1 ng/mL. Overnight cultures from various solid and liquid media proved suitable for PVL detection.

600 strains and clinical isolates from patients from America, Europe, Australia, Africa and the Middle East were tested. Isolates were genotyped in parallel by DNA microarray hybridization for confirmation of PVL status and assignment to clonal complexes. The sensitivity, specificity, positive and negative predictive values of the assay in this trial were 99.7%, 98.3%, 98.4% and 99.7% respectively. 302 clinical isolates and reference strains were PVL positive and were assigned to 21 different clonal complexes.

In summary, the lateral flow test allows rapid and economical detection of PVL in a routine bacteriology laboratory. As the test utilizes cultures from standard media and does not require sophisticated equipment, it can be easily integrated into a laboratory's workflow and might contribute to timely therapy of PVL-associated infections.

The following materials and methods were utilized.

Recombinant PVL, F-component

The PVL F-component gene (lukF-PV) was amplified using primers designed to include an EcoR1 restriction site and a Not1 restriction site at the 5' and 3' end (lukF-PV_fw_5Eco, CCTGAATTCATGAAAAAAATAGTCAAATC (SEQ ID NO: 13) and lukF-PV_rev_5Not, ATAGCGGCCGCTTAGCTCATAGGATTTT (SEQ ID NO: 14)). DNA from the fully sequenced ST1-MRSA-IV reference strain MW2 was used as template. PCR products were cloned into a commercially available vector (TOPO II, Invitrogen, Karlsruhe, Germany) and sequenced. Resulting sequences were compared with the corresponding GenBank entry (BA000033.2; 1529381:153035). Confirmed clones were cut with EcoR1/Not1 and the DNA fragments containing the open reading frame were inserted into the pet28a expression vector (Novagen, Darmstadt, Germany). After ligation, the expression vector was transformed into the E. coli strain BL21. Expression of recombinant proteins was achieved in 50 mL lysogeny broth-medium (LB-medium, supplemented with Kanamycin) after induction with 50 mL isopropyl b-D-1-thiogalactopyranoside (IPTG, 1 mM). E. coli cells were collected by centrifugation and frozen overnight. Expressed recombinant proteins were purified on nickel-nitrilotriacetic acid-agarose (Ni-NTA-agarose) columns (Qiagen, Hamburg, Germany) following manufacturer's instructions. Aliquots were taken after each step and analyzed by sodium dodecyl sulfate-polyacrylamide gel electrophoresis for the presence of the recombinant protein. Protein concentrations of each sample were determined using the bicinchoninic acid (BCA) protein assay kit (Pierce, Bonn, Germany).

Phage Display Procedures and Initial Testing of Antibodies

Over-expressed PVL F-component was used to generate monoclonal antibodies via phage display. Following immunization of mice, mRNA from B-cells was isolated and amplified. Resulting cDNA, specific for the antigen-binding parts of antibodies, was ligated into bacteriophages and then transformed into E. coli. Resulting antibodies were purified, characterized initially by ELISA and different dilutions were spotted onto microtiterstrip-mounted protein microarrays.

Antibody microarrays were used according to previously described protocols.

For the selection of the optimal combination of capture and labeling antibodies, five different concentrations of each of the eleven selected antibodies were spotted onto protein microarrays. These arrays were tested with recombinant PVL F-component, native PVL (in two different concentrations, from the CC30-MSSA strain ATCC25923) or "bovine leukocidin" lukM/lukF-P83 (from a veterinary CC151/705 isolate) as antigens as well as with biotin-labeled preparations of all eleven antibodies as detection antibodies in order to test all possible combinations. Staining was then performed by streptavidin-horseradish peroxidase conjugate and by peroxidase-triggered dye precipitation.

This approach allowed the determination of the optimal combination of capture and detection antibodies (see FIG. 3).

Principles of the Lateral Flow Assay for PVL

The lateral flow assay to detect PVL from primary cultures of S. aureus is an immunochromatographic membrane assay that uses the two highly sensitive phage display recombinant monoclonal antibodies selected by the microarray described above. The two selected antibodies against PVL were used to design a lateral flow test where one of the antibodies is used as the antigen capture on the test strip while the second is gold labeled and coated in a reaction tube. The test strip consists of the PVL capture antibody and control protein immobilized onto a membrane support forming two distinct lines with the addition of a sample and absorbent pad. When performing the test, S. aureus isolates or culture supernatants are added to the coated reaction tube containing the gold conjugate to which an extraction reagent has been added. A PVL assay test strip is then placed into the reaction tube holding the liquid sample and conjugate. Test results are interpreted after 10 minutes based on the presence or absence of pink-to-purple colored sample lines. Two bands (PVL line and control line) indicate a valid positive result, where one band (control line) indicates a valid negative result. The absence of a visible control line was interpreted as an invalid test.

Performing the Assay

The test was applied to isolates of S. aureus from SSTI (see below) that also were genotyped by microarray hybridization to determine strain and clonal complex affiliation and their PVL-status. Specifically, 280 μl of extraction reagent were added to the coated reaction tube containing lyophilized antibody-Au-conjugate. An inoculation loop of S. aureus colony material (approximately 10 μl) was harvested, placed into the tube and thoroughly mixed using the inoculation loop until both cells and conjugate pellet were completely dissolved. When using liquid growth media, 200 μl of buffer and 100 μl of overnight liquid culture were added to the reaction tube and mixed. The test strip was then inserted into the reaction tube. After ten minutes incubation at room temperature, the test strip was withdrawn from the tube and read.

Strains and Isolates

A total of 600 S. aureus strains and isolates were tested for lukF-PV production, including both methicillin-susceptible (MSSA) and methicillin-resistant S. aureus (MRSA).

PVL-negative reference strains were Sanger MSSA476 (a sequenced ST1-MSSA-SCC/us, GenBank accession number BX571857.1), Mu50 and N315 (both sequenced ST5-MRSA-II, GenBank BA000017.4 and BA000018.3), NCTC 8325 (a sequenced ST8-MSSA, GenBank CP000253.1), COL (a sequenced CC8/ST250-MRSA-I, GenBank CP000046.1) as well as West Australian (WA) MRSA-8 (ST75-MRSA-IV 03-17848; (23)) and WA-MRSA-59 (a CC12-MRSA with an atypical SCCmec element).

PVL-positive reference strains were MW2-USA400 (a sequenced ST1-MRSA-IV, GenBank BA000033.2), USA300-FPR3757 (a sequenced ST8-MRSA-IV, GenBank CP000255.1), ATCC25923 (a historic ST30-MSSA isolate widely used in diagnostic microbiology for quality control purposes, Queensland caMRSA (ST93-MRSA-IV 03-16790) and the WA-MRSA-60/Bengal Bay caMRSA (ST772-MRSA-V).

In addition, 588 clinical isolates were included that were collected from patients with SSTI.

The clinical isolates originated from Australia (as part of the countrywide Australian Group for Antimicrobial Resistance Staphylococcus aureus Surveillance Programs SAP2008 and SAP 2010 (available on the world wide web at agargroup.org/files/FED%20REPORT%20SAP2008% 20MRSA%20final.pdf and agargroup.org/files/ FED%20REPORT%20SAP210%20MRSA% 20FINAL%20shrink.pdf). Further isolates came from diagnostic laboratories in Germany (University Hospital Dresden), Saudi-Arabia (King Fahad Medical City, Riyadh), Spain (Hospital Universitari Germans, Trias i Pujol, Badalona), Sweden (Oerebro University Hospital), Trinidad & Tobago (from various regional hospitals in the country), Uganda (Medical Research Council in Entebbe) and England (including a hospital in the South West, Bristol, and the national Staphylococcus Reference Unit, HPA, London). The PVL status of all the isolates from England and of 17 from other countries (eight from Saudi Arabia, seven from Germany, three from Australia) was known. These isolates were included to maximize representation of a broad range of clonal complexes, but were excluded from analysis of PVL rates in the different countries of origin.

In addition, seventeen isolates were tested for LukF-P83; including 14 lukM/lukF-P83 positive isolates from veterinary sources (cattle and goats) belonging to livestock-associated lineages CC 133, CC151/705 and CC479. These isolates were from a previous study, or were referred from the Friedrich Loeffler Institute, Jena, Germany. For control purposes, three lukM/lukF-P83 negative isolates were included: two CC 133 isolates, one from a mute swan, and one from a human from Dresden University Hospital; and a CC479 isolate from cattle. No lukF-P83-negative CC151/705 isolates were available for testing.

Validation of the Lateral Flow Assay Using Different Culture Media.

Liquid growth media included Glucose bouillon (OXOID, Catalogue Nr. CM 67 plus glucose), Brain-Heart infusion (OXOID, CM 225), 2×TY (Tryptone Peptone/Yeast extract), Schaedler bouillon+Vitamin K3 (bioMerieux, 42106) and a broth described by Kato and Noda.

The following solid media were used: plain agar (OXOID, CM3), Mueller Hinton agar (OXOID, CM337) with and without blood added, Columbia Blood (agar basis OXOID, CM331 and sheep blood OXOID, FSR1055), C A P. agar, "chocolate" agar (agar basis OXOID, CM331 and sheep blood OXOID FSR1055 plus Haemin, Serva, 24410, and NAD, Merck, 1.024542) and commercially available chromogenic MRSA medium (MRSA ID agar, bioMerieux, 43459).

Array Procedures

For confirmation of PVL status and for assignment to clonal complexes and strains, all isolates were characterized by DNA microarray hybridization (StaphyType™ by Alere, Jena). The procedure was carried out in accordance with manufacturer's instructions; primers, probes and further details have been described previously.

Briefly, DNA was prepared following enzymatic lysis. A multiplex primer elongation was performed that amplified and labeled (by incorporation of biotin-16-dUTP) a total of 333 target sequences corresponding to ca. 170 genes. Single stranded amplification products were hybridized against microarrays on which the corresponding probes were spotted. Hybridizations were visualized by adding a streptavidin-horseradish peroxidase conjugate that binds to the biotin tags, and by a peroxidase-triggered dye precipitation. The resulting pattern of spots on the array was scanned, analyzed and compared to a reference database of previously typed strains. Full hybridization profiles of all strains and isolates are provided in the supplemental file.

The following experimental results were obtained.

Antibody Screening

Based on the screening results shown in FIG. 3, a combination of Antibody 1401 (also referred to herein as PVL-1401) and Antibody 1841 (also referred to herein as PVL-1841) was selected to establish a lateral flow assay capable of detecting PVL (F-component) as well as the gene product of lukF-P83. The detection limit for the lateral flow test with purified native and recombinant antigen was determined by dilution series to be approximately 1 ng/mL.

Tests of the Lateral Flow Test With Different Growth Media

In the first series of experiments, known strains cultured on different growth media were tested. Liquid growth media (Glucose bouillon, Brain-Heart infusion, 2×TY, Schaedler and Kato & Noda) were tested with PVL-negative Mu50 (ST5-MRSA-II), NCTC8523 (ST8-MSSA) and known isolates of ST398-MRSA-V and ST8-MSSA as well as with PVL-positive USA300-FPR3757 (ST8-MRSA-IV, USA300) and isolates of CC30-MSSA and ST93-MRSA-IV (Queensland clone). The PVL-negative ST8-MSSA strain NCTC8325 gave weak but consistent false-positive results in the growth medium as described by Kato & Noda. This was not observed using genotypically identical clinical isolates of ST8-MSSA. All other results were correct.

Colony material (of PVL-positive ST22-MRSA-IV and of USA300-FPR3757) harvested from plain Agar, Mueller Hinton agar with and without blood, Columbia Blood, C.A.P. and "chocolate" agar yielded correct positive results. Screening of clinical isolates (see below) was then performed using overnight colonies from Columbia Blood agar.

In addition to the aforementioned growth media, a commercially available chromogenic medium for MRSA detection was tested (MRSA ID agar by bioMerieux). Following PVL-positive strains were tested and yielded correct results:

CC1-MRSA-IV (MW2, USA400), CC5-MRSA-IV, ST8-MRSA-IV (USA300-FPR3757), ST22-MRSA-IV, ST30-MRSA-IV (Southwest Pacific clone), ST59/ST952-MRSA-V(T) (Taiwan clone), CC80-MRSA-IV (European caMRSA clone), CC88-MRSA-IV and CC152-MRSA-V. PVL-negative strains CC1-MRSA-IV&SCC/us (WA-MRSA-1/45), ST22-MRSA-IV (UK-EMRSA-15/Barnim), ST45-MRSA-IV (Berlin EMRSA), ST75-MRSA-IV (WA-MRSA-8), ST239-MRSA-III (Vienna/Hungarian/Brazilian epidemic strain) and a PVL-negative variant of CC80-MRSA-IV from MRSA ID agar yielded accurate (negative) results.

Detection of LukF-P83

The fourteen lukF-P83-positive isolates (two CC 133, four CC479 and eight CC151) yielded positive results in the lateral flow assay. The three lukF-P83-negative isolates (two CC 133 and one CC479) were correctly identified as negative.

Screening of Clinical Isolates Using the Lateral Flow Test and the Microarray

When compared to the array based genotyping data, 301 experiments were true positives and 293 were true negatives; there were five false positives, and one false negative. This corresponds to a sensitivity of 99.7%, a specificity of 98.3%, a PPV of 98.4% and a NPV of 99.7%. The six experiments with false results were repeated subsequently and yielded correct results suggesting operator errors on primary testing.

Overall, 297 test isolates and five reference strains were PVL positive. By array hybridizations, they were assigned to 21 different clonal complexes, CC1 (including ST772), CC5, CC8 (including ST72), CC15, CC22, CC25, CC30, CC45, CC49, CC59, CC80, CC88, CC93, CC96, CC121, CC 152, CC 188, CC398 and three unidentified lineages (FIG. 13). One of them yielded a MLST profile of 1-141-1-1-128-3 (related to STs 1279/1496/1982). The most frequently isolated PVL-positive lineages were CC12 (50 isolates from different regions, all MSSA), CC30 (46 isolates; MSSA and MRSA with SCCmec IV elements), CC8 (46 isolates including MSSA from Trinidad & Tobago as well as "USA300" from various regions) and CC93 (42 isolates, MSSA and ST93-MRSA-IV, Queensland caMRSA clone, almost exclusively from Australia). The 287 PVL-negative test isolates and seven reference strains were assigned to 31 different clonal complexes; CC1, CC5, CC6, CC7, CC8 (including ST72 and ST239), CC9 (ST834), CC12, CC15, CC20, CC22, CC25, CC30 (including ST34), CC45, CC50, CC59, CC75, CC80, CC88, CC96, CC97, CC101, CC121, CC140, CC188, CC398, CC425, CC509, CC707 and CC1021. Two isolates could not be allocated to a CC.

Prevalence of PVL Positive S. aureus in Different Countries

The prevalence of PVL-positive isolates among all SSTI isolates varied widely between the different countries. The highest rate of PVL positives was observed among the Australian samples, with 82.2% (74 of 90) being PVL-positive. Half of PVL-positive isolates (37 of 74) belonged to CC93, and the majority of them were MRSA (29 of 37 CC93 isolates, 78%), reflecting the burden the so-called Queensland caMRSA clone currently poses. The second and third most frequently isolated PVL-positive clones in Australia were CC121-MSSA (n=15) and CC93-MSSA (n=8). Only two isolates of ST8-MRSA-IV (USA300) were identified. PVL-negative S. aureus isolates were from multiple CC lineages including CCI, CC5, CC8, CC8/ST72, CC15, CC22, CC30, CC45, CC88 and CC188 and included two MRSA clones; ST22-MRSA-IV (UK-EMRSA-15/Barnim EMRSA) and ST5-MRSA-IV (Pediatric clone/WA-MRSA-65).

Among SSTI isolates from Germany, the PVL rate was 40% (20 of 50). The most common strains were CC121-MSSA (n=7) and CC30-MSSA (n=4). One each of ST8-MRSA-IV (USA300) and ST93-MRSA-IV (Queensland caMRSA clone) were identified, the latter being associated with travel to Australia. Among the PVL-negatives, CC30 and CC8 were the most frequently isolated; other CCs included CC5, CC7, CC8/ST72, CC15, CC22, CC45, CC101 and CC398. Single isolates of PVL-negative MRSA belonged to CC7-MRSA-IV, CC22-MRSA-IV (UK-EMRSA-15/Barnim EMRSA), ST5/ST225-MRSA-II (UK-EMRSA-3/Rhine-Hesse EMRSA) and CC45-MRSA-IV (Berlin EMRSA) were identified.

Of the isolates from Saudi Arabia, 47.3% (24 of 53) from proved to be positive for PVL. Roughly half were MRSA (n=13) with the single most common PVL-positive clone being CC80-MRSA-IV (European caMRSA clone; 10 isolates). The most frequently isolated PVL-MSSA clones were CC30-MSSA (n=4) and a yet unidentified MSSA (n=3). PVL negatives belonged to CC1, CC5, CC6, CC7, CC8, CC9/ST834, CC15, CC22, CC25, CC30, CC45, CC75 (related to ST1667), CC80, CC96, CC97, CC398 (ST291/813), and one unidentified lineage. The proportion of MRSA was high (8 of 29 PVL-negatives); the most common strain being ST239-MRSA-III (Vienna/Hungarian/Brazilian clone, n=4). Other MRSA belonged to a tstI—positive variant of CC22-MRSA-IV, a PVL-negative variant of CC80-MRSA-IV, a CC5-MRSA-IV&SCC/us strain previously known only from Malta (27) and CC9/ST834-MRSA-VI.

The second highest PVL rate was found in Spain, with 75% (33 of 44) being positive for PVL genes as well as for secreted LukF-PV protein. Here, the most common clone was an ACME-negative variant of ST8-MRSA-IV (USA300), to which 10 isolates were assigned. This was followed by CC30-MSSA (n=6) and CC22-MSSA (n=5). The PVL-negatives belonged to a variety of CCs (CC5, CC8/ST72, CC 15, CC30, CC45, CC121, CC188 and CC707) and did not include any MRSA.

The lowest prevalence for PVL was observed among the Swedish isolates. Only 16.7% (19 of 114) were PVL-positive, all MSSA. The most common PVL-positive strains were CC30-MSSA (n=4) and CC121-MSSA (n=3). PVL negative isolates were CC1, CC5, CC7, CC8, CC12, CC15, CC20, CC22, CC30, CC45, CC50, CC88, CC97, CC101, CC121, CC188, CC509 and CC1021. CC45 (n=19) and CC15 (n=18) were the most frequently isolated CCs. MRSA were not found.

In Trinidad & Tobago, the PVL prevalence was 50% (40 of 80 isolates). The most abundant PVL-positive strain was CC8-MSSA (n=18) that additionally carried enterotoxin genes sed, sej, ser, sek and seq. Two CC8-MRSA-IV isolates were identified with the same toxin profile, but lacked ACME and thus resembled WA-MRSA-62. ST8-MRSA-IV (USA300), i.e. carrying the ACME locus and enterotoxin genes sek and seq, was identified in three cases. Other frequently isolated PVL-positive strains were CC30-MSSA (n=10) and CC5-MSSA (n=5). PVL negative isolates included CC1, CC6, CC7, CC8, CC8/ST72, CC8/ST239, CC12, CC15, CC45, CC59, CC101, CC121, CC188 and unusual strains related to CC75 (ST1223, ST1667). The PVL negative MRSA strains were CC59-MRSA-V&SCC/us and ST239-MRSA-III (Vienna/Hungarian/Brazilian clone).

In Uganda, 30.6% (19 of 62) were PVL-positive, including 17 isolates belonging to CC121-MSSA and single representatives of CC30- and CC80-MSSA. PVL-positive MRSA was not identified. PVL negative strains belonged to CC1, CC5, CC8, CC8/ST72, CC8/ST239, CC9, CC15, CC25, CC121, ST140 and to an unidentified lineage. The most common lineage was CC8 (n=22, plus one isolate of CC8/ST72 and CC8/ST239). PVL-negative MRSA included two of ST140-MRSA-IV isolates as well as single isolates of CC5-MRSA-IV (Pediatric clone) and ST239-MRSA-III (Vienna/Hungarian/Brazilian clone).

In contrast to the collections from other countries, the PVL status of the isolates from England were already known, thus the PVL rates cannot be compared to those of the other countries. A variety of different PVL-MRSA strains was identified among the London isolates, CC30-MRSA-IV (Southwest Pacific caMRSA clone), CC5-MRSA-IV (Pediatric clone), CC5-MRSA-V, CC80-MRSA-IV (European caMRSA clone), ST59/ST952-MRSA-V(T) (Taiwan caMRSA clone), ST772-MRSA-V (Bengal Bay caMRSA clone/WA-MRSA-60), ST8-MRSA-IV (USA300) and ST93-MRSA-IV (Queensland caMRSA clone). PVL negative isolates belonged to CC1, CC8, CC8/ST239, CC12, CC22, CC25, CC30, CC45, CC59, CC121, CC425 including MRSA strains CC1-MRSA-IV (WA-MRSA-1/57), ST239-MRSA-III (Vienna/Hungarian/Brazilian clone), CC22-MRSA-IV (UK-EMRSA-15/Barnim EMRSA) and ST59-MRSA-V. A further 28 isolates were included from a second centre in the South West of England that were already known to be PVL-positive. These were also excluded from the analysis of PVL rates, but their population structure was notable. This group included only two PVL-positive MRSA, ST772-MRSA-V (Bengal Bay caMRSA clone/WA-MRSA-60) and CC1-MRSA-IV (USA400). It also included one CC59-MSSA that probably was a SCCmec-deletion mutant of ST59/ST952-MRSA-V(T) (Taiwan caMRSA clone), based on the hybridization profile with regard to resistance genes and virulence markers (erm(B), apha3, sat, tet(K), cat, fexA, seb/k/q, lukF/S-PV). The most common strain in this group was a PVL-positive CC22-MSSA (n=10). Another five PVL-positive CC22 isolates with spa types t417 or t1601 carried "SCCfus" elements (ccrA/B-1, and Q6GD50, or fusC). These isolates originated from patients with an average age of nearly 94 years. This is an unusual finding among PVL-positives and suggests a possible association of this clonal complex with care facilities in this regionPVL is a unique virulence marker in S. aureus and it is most commonly associated with clinical symptoms which tend to be either chronic/recurrent or, occasionally, rapidly progressing and life-threatening. A diagnostic test for PVL would be thus desirable for targeted patient management. The lateral flow assay described herein allows the rapid detection of PVL in a routine bacteriological laboratory that is not able to readily perform molecular assays. As it utilizes pure overnight cultures from standard media, such as Columbia Blood Agar, it can easily be integrated into a routine diagnostic laboratory workflow. Thus the assay might contribute to timely therapeutic interventions in cases of PVL-associated infections, and it also might help to select isolates for submission for further typing in reference centers The amount of PVL released by S. aureus in vitro varies widely, however the high concordance between the genotypic and phenotypic assays suggests lukS/F-PV positive strains generally express detectable amounts of PVL using standard culture conditions. In this study no isolates were identified that harbored PVL genes without producing the toxin in vitro. The probability of false-negative results due to a lack of expression in vitro is low. The diversity of PVL- and lukM/lukF-P83 positive strains included in this study indicate that possible lineage-specific variations in PVL sequences do not pose an obstacle to PVL detection by the antibodies described herein. Further, the collection of isolates described herein provides a snapshot of the molecular epidemiology of S. aureus associated with SSTI. Among the PVL-positive methicillin-susceptible S. aureus, CC121 (50 isolates in total) and CC30 (35 isolates) dominated. PVL-positive CC8-MSSA was abundant in Trinidad & Tobago although this strain was rare elsewhere. This lends credence to the hypothesis that the USA300 strain emerged in the Caribbean/Latin American region. The study also shows MRSA poses a serious problem in different parts of the world. The countries with low prevalence or absence of MRSA (in this study) were Sweden, which has a very strict policy on MRSA infection control, and Uganda, where selective pressure on S. aureus by the use of antibiotics in healthcare and veterinary medicine may be more limited than in other countries. Elsewhere, MRSA was isolated frequently, with PVL-positive/ACME-positive ST8-MRSA-IV (USA300), PVL-positive/ACME-negative ST8-MRSA-IV, PVL-positive ST80-MRSA-IV (European caMRSA clone) and ST93-MRSA-IV (Queensland caMRSA clone) and PVL-negative ST239-MRSA-III dominating. The possibility of combining the lateral flow assay with a chromogenic MRSA screening medium facilitates a quick screening for emerging strains of PVL-positive caMRSA. This could be helpful to arrest their dissemination and further expansion. The high percentage of PVL-positives among Australian and Spanish isolates and the predominance of ST93-MRSA-IV (Queensland caMRSA clone) and ST8-MRSA-IV in these two countries suggest that an expansion of PVL-positive caMRSA does not occur at the expense of the established PVL-positive MSSA populations, but in addition to it. Besides limiting the efficacy of beta-lactams as primary therapeutic option, the emergence of PVL-positive caMRSA may thus result in an increased burden of PVL-associated disease. Although the number of isolates in the present study is not sufficient to unambiguously prove such a trend, it warrants further study with respect to the molecular epidemiology of PVL-positive S. aureus.

The invention illustratively described herein may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

While the disclosure has been particularly shown and described with reference to several embodiments thereof with particular details, it will be apparent to one of ordinary skill in the art that various changes may be made to these embodiments without departing from the principles and spirit of the invention, the scope of which is defined in the following claims and their equivalents.

What is claimed is:

1. A method of detecting a biomolecule in a sample, comprising:
   a) contacting a sample with an antibody, or a functional binding fragment thereof, that specifically binds an expression product of one or more genes selected from lukS-PV, lukF-PV, lukM, lukF-P83, mecA, and spa, to form a conjugate; and
   b) detecting the conjugate of (a), thereby detecting the toxin,
wherein the antibody, or the functional binding fragment thereof, comprises an amino acid sequence as set forth in SEQ ID NOs: 2, 4, 6, 8, 10 or 12.

2. The method of claim 1, wherein the antibody, or the functional binding fragment thereof, is clone PVL-1841, clone PVL-1321, or clone PVL-1401.

3. The method of claim 1, wherein the sample is contacted with an antibody, or a functional binding fragment thereof, selected from at least two of clone PVL-1841, clone PVL-1321, and clone PVL-1401.

4. The method of claim 1, wherein the antibody, or the functional binding fragment thereof, further comprises one or more of PVL-1031, PVL-1061, PVL-1101, PVL-1451, PVL-1631, PVL-1711, PVL-1771, PVL-1881, PBP2a-1631, PBP2a-1721, PBP2a-1941, PBP2a-6G10, PBP2a-17A10, PBP2a-17C8, PBP2a-19B1, PBP2a-8A5, PBP2a-9C6, PBP2a-pc-2.1, PBP2a-pc-2.2, SPA-A135, and SPA-4412.

5. The method of claim 1, wherein the antibody, or the functional binding fragment thereof, further comprises at least two of PVL-1031, PVL-1061, PVL-1101, PVL-1451, PVL-1631, PVL-1711, PVL-1771, PVL-1881, PBP2a-1631, PBP2a-1721, PBP2a-1941, PBP2a-6G10, PBP2a-17A10, PBP2a-17C8, PBP2a-19B1, PBP2a-8A5, PBP2a-9C6, PBP2a-pc-2.1, PBP2a-pc-2.2, SPA-A135, and SPA-4412.

6. The method of claim 1, wherein the function binding fragment is selected from the group consisting of an Fab, F(ab')2, Fd, Fv, and combinations thereof.

7. The method of claim 1, wherein the antibody is conjugated to a detectable label.

8. The method of claim 7, wherein the label is a metal particle.

9. The method of claim 8, wherein the metal is gold.

10. The method of claim 1, wherein the sample comprises the expression product from pre-cultured *S. aureus* cells.

11. The method of claim 10, wherein the culture media is a liquid or a solid media.

12. The method of claim 1, further comprising contacting the sample with an antibody, or a functional binding fragment thereof, that specifically binds to PVL, penicillin-binding protein 2a (PBP2a), protein A (spa), or any combination thereof.

13. The method of claim 1, wherein (a) is performed on an immunoassay device or a microarray.

14. The method of claim 1, wherein the immunoassay device is a lateral flow immunoassay device.

* * * * *

SEQUENCE LISTING

<160> NUMBER OF SEQ ID NOS: 14

<210> SEQ ID NO 1
<211> LENGTH: 660
<212> TYPE: DNA
<213> ORGANISM: Artificial Sequence
<220> FEATURE:
<223> OTHER INFORMATION: Synthetic construct

<400> SEQUENCE: 1

```
gacgttgtga tgtcacagtc tccatcctcc ctgactgtga cagcaggaga gaaggtcact    60
atgagctgca agtccagtca gagtctgtta ctcagtggaa atcaaaagaa cctcttgacc   120
tggttccagc agaaaccagg gcagcctcct aaactgttga tctactgggc atccactagg   180
gaatctgggg tccctgatcg cttcacaggc agtggatctg gaacagattt cactctcacc   240
atcagcagtg tgcaggctga agacctggca gtttattact gtcagaatga ttataattat   300
ccgtacacgt tcggagggg gaccaagctg aaataaaac gggctgatgc tgcaccaact   360
gtatccatct tcccaccatc cagtgagcag ttaacatctg gaggtgcctc agtcgtgtgc   420
ttcttgaaca acttctaccc caaagacatc aatgtcaagt ggaagattga tggcagtgaa   480
cgacaaaatg gcgtcctgaa cagttggact gatcaggaca gcaaagacag cacctacagc   540
atgagcagca ccctcacgtt gaccaaggac gagtatgaac acataacag ctatacctgt   600 gaggccactc acaagacatc aacttcaccc attgtcaaga gcttcaacag gaatgagtct   660
```

<210> SEQ ID NO 2
<211> LENGTH: 220
<212> TYPE: PRT
<213> ORGANISM: Artificial Sequence
<220> FEATURE:
<223> OTHER INFORMATION: Synthetic construct

<400> SEQUENCE: 2

```
Asp Val Val Met Ser Gln Ser Pro Ser Ser Leu Thr Val Thr Ala Gly
1               5                   10                  15

Glu Lys Val Thr Met Ser Cys Lys Ser Ser Gln Ser Leu Leu Leu Ser
            20                  25                  30

Gly Asn Gln Lys Asn Leu Leu Thr Trp Phe Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Asn Tyr Pro Tyr Thr Phe Gly Gly Gly Thr Lys Leu Glu Ile
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
            180                 185                 190
```

Glu Arg His Asn Ser Tyr Thr Cys Glu Ala Thr His Lys Thr Ser Thr
        195                 200                 205

Ser Pro Ile Val Lys Ser Phe Asn Arg Asn Glu Ser
    210                 215                 220

<210> SEQ ID NO 3
<211> LENGTH: 681
<212> TYPE: DNA
<213> ORGANISM: Artificial Sequence
<220> FEATURE:
<223> OTHER INFORMATION: Synthetic construct

<400> SEQUENCE: 3

```
caggtccagc tgcagcagtc tgggcctcag ctggttaggc ctggggcttc agtgaagata     60
tcctgcaagg cttctggtca ctcattcacc acctactgga tgcactgggt gaagcagagg    120
cctggacaag gtcttgagtg gattggcatg attgatcctt ccgatagtga aactaggtta    180
aatcagaagt tcaaggacaa ggccacattg actgtagaca atcctccag cacagtctac     240
atgcaactca gcagcccgac atctgaagac tctgtggtct attactgtgc aagctactat    300
ggcaattcta tggactactg gggtcaagga acctcagtca ccgtctcctc agccaaaacg    360
acacccccat ctgtctatcc actggcccct ggatctgctg cccaaactaa ctccatggtg    420
accctgggat gcctggtcaa gggctatttc cctgagccag tgacagtgac ctggaactct    480
ggatccctgt ccagcggtgt gcacaccttc ccagctgtcc tgcagtctga cctctacact    540
ctgagcagct cagtgactgt cccctccagc acctggccca gcgagaccgt cacctgcaac    600
gttgcccacc cggccagcag caccaaggtg gacaagaaaa ttgtgcccag ggattgtcat    660
catcaccatc accatcacta a                                              681
```

<210> SEQ ID NO 4
<211> LENGTH: 226
<212> TYPE: PRT
<213> ORGANISM: Artificial Sequence
<220> FEATURE:
<223> OTHER INFORMATION: Synthetic construct

<400> SEQUENCE: 4

Gln Val Gln Leu Gln Gln Ser Gly Pro Gln Leu Val Arg Pro Gly Ala
1               5                   10                  15

Ser Val Lys Ile Ser Cys Lys Ala Ser Gly His Ser Phe Thr Thr Tyr
            20                  25                  30

Trp Met His Trp Val Lys Gln Arg Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60

Lys Asp Lys Ala Thr Leu Thr Val Asp Lys Ser Ser Ser Thr Val Tyr
65                  70                  75                  80

Met Gln Leu Ser Ser Pro Thr Ser Glu Asp Ser Val Val Tyr Tyr Cys
                85                  90                  95

Ala Ser Tyr Tyr Gly Asn Ser Met Asp Tyr Trp Gly Gln Gly Thr Ser
            100                 105                 110

Val Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser

```
145                 150                 155                 160
Gly Ser Leu Ser Ser Gly Val His Thr Phe Pro Ala Val Leu Gln Ser
                165                 170                 175

Asp Leu Tyr Thr Leu Ser Ser Val Thr Val Pro Ser Ser Thr Trp
            180                 185                 190

Pro Ser Glu Thr Val Thr Cys Asn Val Ala His Pro Ala Ser Ser Thr
            195                 200                 205

Lys Val Asp Lys Lys Ile Val Pro Arg Asp Cys His His His His
        210                 215                 220

His His
225

<210> SEQ ID NO 5
<211> LENGTH: 657
<212> TYPE: DNA
<213> ORGANISM: Artificial Sequence
<220> FEATURE:
<223> OTHER INFORMATION: Synthetic construct

<400> SEQUENCE: 5
gatgttgtgg tgactcaaac tccactctcc ctgcctgtca gtcttggaga tcaagcctcc      60
atctcttgca gatctagtca gagccttgta cacagtgatg aaacaccta tttacattgg     120 tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgaaga tctgggagtt tatttctgct ctcaaaatac acatgttcca     300
ttcacattcg gctcggggac aaagttggaa ataaaacggg ctgatgctgc accaactgta     360
tccatcttcc caccatccag tgagcagtta acatctggag gtgcctcagt cgtgtgcttc     420
ttgaacaact ctaccccaa agcatcaat gtcaagtgga gattgatgg cagtgaacga     480 caaaatggcg tcctgaacag ttggactgat caggacagca agacagcac ctacagcatg     540 agcagcaccc tcacgttgac caaggacgag tatgaacgac ataacagcta cctgtgag      600 gccactcaca gacatcaac ttcacccatt gtcaagagct tcaacaggaa tgagtct       657

<210> SEQ ID NO 6
<211> LENGTH: 219
<212> TYPE: PRT
<213> ORGANISM: Artificial Sequence
<220> FEATURE:
<223> OTHER INFORMATION: Synthetic construct

<400> SEQUENCE: 6

Asp Val Val Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Phe Thr Phe Gly Ser Gly Thr Lys Leu Glu Ile Lys
            100                 105                 110
```

```
Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Ser
        210                 215
```

<210> SEQ ID NO 7
<211> LENGTH: 681
<212> TYPE: DNA
<213> ORGANISM: Artificial Sequence
<220> FEATURE:
<223> OTHER INFORMATION: Synthetic construct

<400> SEQUENCE: 7

```
gagatccagc tgcagcagtc tggagctgag ctggggaggc ctgggtcctc agtgaagctg    60
tcctgcaaga cttctggata ctttcaca aactttttata taacctggct gaaacagagg    120
cctggacagg gcctggaatg gattggattt atttatcctg gaaatggtta tactgcatac   180
aatgagaaat tccagggaga ggccacactg acttcagaca tcttccag cacagcctac     240
atgcacctca aagcctgac atctgaggac tctgcaatct atttctgtgc aagactggga    300
cgaaatgaag ttgactactg gggccaaggc accactctca cagtctcctc agccaaaacg   360
acaccccat ctgtctatcc actggccct ggatctgctg cccaaactaa ctccatggtg     420
accctgggat gcctggtcaa gggctatttc cctgagccag tgacagtgac ctggaactct   480
ggatccctgt ccagcggtgt gcacaccttc cagctgtcc tgcagtctga cctctacact    540
ctgagcagct cagtgactgt cccctccagc acctggccca gcgagaccgt cacctgcaac   600
gttgcccacc cggccagcag caccaaggtg gacaagaaaa ttgtgcccag ggattgtcat   660
catcaccatc accatcacta a                                              681
```

<210> SEQ ID NO 8
<211> LENGTH: 226
<212> TYPE: PRT
<213> ORGANISM: Artificial Sequence
<220> FEATURE:
<223> OTHER INFORMATION: Synthetic construct

<400> SEQUENCE: 8

```
Glu Ile Gln Leu Gln Gln Ser Gly Ala Glu Leu Gly Arg Pro Gly Ser
1               5                   10                  15

Ser Val Lys Leu Ser Cys Lys Thr Ser Gly Tyr Thr Phe Thr Asn Phe
            20                  25                  30

Tyr Ile Thr Trp Leu Lys Gln Arg Pro Gly Gln Gly Leu Glu Trp Ile
        35                  40                  45

Gly Phe Ile Tyr Pro Gly Asn Gly Tyr Thr Ala Tyr Asn Glu Lys Phe
    50                  55                  60

Gln Gly Glu Ala Thr Leu Thr Ser Asp Thr Ser Ser Ser Thr Ala Tyr
```

```
                65                  70                  75                  80
Met His Leu Arg Ser Leu Thr Ser Glu Asp Ser Ala Ile Tyr Phe Cys
                    85                  90                  95
Ala Arg Leu Gly Arg Asn Glu Val Asp Tyr Trp Gly Gln Gly Thr Thr
                100                 105                 110
Leu Thr Val Ser Ser Ala Lys Thr Thr Pro Pro Ser Val Tyr Pro Leu
            115                 120                 125
Ala Pro Gly Ser Ala Ala Gln Thr Asn Ser Met Val Thr Leu Gly Cys
        130                 135                 140
Leu Val Lys Gly Tyr Phe Pro Glu Pro Val Thr Val Thr Trp Asn Ser
145                 150                 155                 160
Gly Ser Leu Ser Ser Gly Val His Thr Phe Pro Ala Val Leu Gln Ser
                165                 170                 175
Asp Leu Tyr Thr Leu Ser Ser Ser Val Thr Val Pro Ser Ser Thr Trp
                180                 185                 190
Pro Ser Glu Thr Val Thr Cys Asn Val Ala His Pro Ala Ser Ser Thr
            195                 200                 205
Lys Val Asp Lys Lys Ile Val Pro Arg Asp Cys His His His His
        210                 215                 220
His His
225

<210> SEQ ID NO 9
<211> LENGTH: 660
<212> TYPE: DNA
<213> ORGANISM: Artificial Sequence
<220> FEATURE:
<223> OTHER INFORMATION: Synthetic construct

<400> SEQUENCE: 9
gacatcgtta tgtctcagtc tccatcctcc ctagctgtgt cagttggaga gacggttact      60
atgagctgca agtccagtca gacccttta tatagtagca atcaaaagaa ttacttggcc     120
tggtaccagc agaaaccagg acagtctcct aaattgctga tttactgggc atccactagg     180
gaatctgggg tcccagatcg cttcacaggc agtggatctg ggacagattt cactctcacc     240
atcagcagtg tgaaggctga agacctggca gtttattact gtcagcaata ttatgactat     300
ccgctcacgt tcggtgctgg gaccaagctg gagctgaaac gggctgatgc tgcaccaact     360
gtatccatct tcccaccatc cagtgagcag ttaacatctg gaggtgcctc agtcgtgtgc     420
ttcttgaaca acttctaccc caaagacatc aatgtcaagt ggaagattga tggcagtgaa     480
cgacaaaatg gcgtcctgaa cagttggact gatcaggaca gcaaagacag cacctacagc     540
atgagcagca ccctcacgtt gaccaaggac gagtatgaac gacataacag ctatacctgt     600
gaggccactc acaagacatc aacttcaccc attgtcaaga gcttcaacag gaatgagtct     660

<210> SEQ ID NO 10
<211> LENGTH: 220
<212> TYPE: PRT
<213> ORGANISM: Artificial Sequence
<220> FEATURE:
<223> OTHER INFORMATION: Synthetic construct

<400> SEQUENCE: 10

Asp Ile Val Met Ser Gln Ser Pro Ser Leu Ala Val Ser Val Gly
1               5                   10                  15
Glu Thr Val Thr Met Ser Cys Lys Ser Ser Gln Thr Leu Leu Tyr Ser
            20                  25                  30
```

Ser Asn Gln Lys Asn Tyr Leu Ala Trp Tyr Gln Gln Lys Pro Gly Gln
                 35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Asp Tyr Pro Leu Thr Phe Gly Ala Gly Thr Lys Leu Glu Leu
                100                 105                 110

Lys Arg Ala Asp Ala Ala Pro Thr Val Ser Ile Phe Pro Pro Ser Ser
                115                 120                 125

Glu Gln Leu Thr Ser Gly Gly Ala Ser Val Val Cys Phe Leu Asn Asn
                130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
                180                 185                 190

Glu Arg His Asn Ser Tyr Thr Cys Glu Ala Thr His Lys Thr Ser Thr
                195                 200                 205

Ser Pro Ile Val Lys Ser Phe Asn Arg Asn Glu Ser
                210                 215                 220

```
<210> SEQ ID NO 11
<211> LENGTH: 684
<212> TYPE: DNA
<213> ORGANISM: Artificial Sequence
<220> FEATURE:
<223> OTHER INFORMATION: Synthetic construct

<400> SEQUENCE: 11
gacgtgcagg tggtggagtc tgggggaggc ttagtgaagc ctggagggtc cctgaaactc      60
tcctgtgcag tctctggatt cactttcagt agttatcaca tgtcttgggt tcgccagact     120
ccggcgaaga ggctggagtg ggtcgcaacc attagtggtg gtggtggtaa cacctactat     180
ccagacagtg tgaagggccg attcaccatc tccagagaca tgccaagaa caccctgttc      240 ctgcaaatga gcagtctgag gtctgaggac acggccttgt attactgtgc aagacatgag     300
ggtccttact actccttcga tgtctggggc acagggacca cggtcaccgt ctcttcagcc     360
aaaacgacac cccatctgt ctatccactg gcccctggat ctgctgccca actaactcc       420 atggtgaccc tgggatgcct ggtcaagggc tatttccctg agccagtgac agtgacctgg     480
aactctggat ccctgtccag cggtgtgcac accttccag ctgtcctgca gtctgacctc      540
tacactctga gcagctcagt gactgtcccc tccagcacct ggcccagcga gaccgtcacc     600
tgcaacgttg cccacccggc cagcagcacc aaggtggaca gaaaaattgt gcccagggat     660
tgtcatcatc accatcacca tcac                                            684

<210> SEQ ID NO 12
<211> LENGTH: 228
<212> TYPE: PRT
<213> ORGANISM: Artificial Sequence
<220> FEATURE:
<223> OTHER INFORMATION: Synthetic construct
```

<400> SEQUENCE: 12

Asp Val Gln Val Val Glu Ser Gly Gly Gly Leu Val Lys Pro Gly Gly
1               5                   10                  15

Ser Leu Lys Leu Ser Cys Ala Val Ser Gly Phe Thr Phe Ser Ser Tyr
            20                  25                  30

His Met Ser Trp Val Arg Gln Thr Pro Ala Lys Arg Leu Glu Trp Val
        35                  40                  45

Ala Thr Ile Ser Gly Gly Gly Asn Thr Tyr Tyr Pro Asp Ser Val
    50                  55                  60

Lys Gly Arg Phe Thr Ile Ser Arg Asp Asn Ala Lys Asn Thr Leu Phe
65              70                  75                  80

Leu Gln Met Ser Ser Leu Arg Ser Glu Asp Thr Ala Leu Tyr Tyr Cys
                85                  90                  95

Ala Arg His Glu Gly Pro Tyr Tyr Ser Phe Asp Val Trp Gly Thr Gly
            100                 105                 110

Thr Thr Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys His His His
    210                 215                 220

His His His His
225

<210> SEQ ID NO 13
<211> LENGTH: 29
<212> TYPE: DNA
<213> ORGANISM: Artificial Sequence
<220> FEATURE:
<223> OTHER INFORMATION: Primer

<400> SEQUENCE: 13
cctgaattca tgaaaaaaat agtcaaatc                                     29

<210> SEQ ID NO 14
<211> LENGTH: 28
<212> TYPE: DNA
<213> ORGANISM: Artificial Sequence
<220> FEATURE:
<223> OTHER INFORMATION: Primer

<400> SEQUENCE: 14
atagcggccg cttagctcat aggattttt                                     28